US008981150B2

(12) United States Patent
Vidal et al.

(10) Patent No.: US 8,981,150 B2
(45) Date of Patent: Mar. 17, 2015

(54) ETHER-AMIDE COMPOUNDS AND USES THEREOF

(75) Inventors: Thierry Vidal, Lyons (FR); Massimo Guglieri, Monaco (MC); Olivier Jentzer, Vourles (FR)

(73) Assignee: Rhodia Operations, Aubervilliers (FR)

( * ) Notice: Subject to any disclaimer, the term of this patent is extended or adjusted under 35 U.S.C. 154(b) by 182 days.

(21) Appl. No.: 13/502,874

(22) PCT Filed: Oct. 18, 2010

(86) PCT No.: PCT/FR2010/052212
§ 371 (c)(1),
(2), (4) Date: Aug. 1, 2012

(87) PCT Pub. No.: WO2011/048314
PCT Pub. Date: Apr. 28, 2011

(65) Prior Publication Data
US 2012/0302791 A1 Nov. 29, 2012

(30) Foreign Application Priority Data

Oct. 19, 2009 (FR) .................................. 09 05000

(51) Int. Cl.
*C07C 271/12* (2006.01)
*C07C 271/24* (2006.01)
*C07C 233/05* (2006.01)
*C07C 235/06* (2006.01)
*A01N 25/02* (2006.01)

(52) U.S. Cl.
CPC .............. *C07C 235/06* (2013.01); *A01N 25/02* (2013.01); *C07C 2101/14* (2013.01)
USPC ...... 564/201; 564/123; 504/339; 106/287.25; 252/364; 508/528; 514/629

(58) Field of Classification Search
CPC .. C07C 233/05; C07C 233/10; C07C 271/12; C07C 271/24
USPC ................. 564/201, 123; 504/339; 71/54; 106/287.25; 252/364; 508/528; 514/629
See application file for complete search history.

(56) References Cited

U.S. PATENT DOCUMENTS

| | | | |
|---|---|---|---|
| 2,447,587 A | 8/1948 | Martin et al. | |
| 3,827,994 A | 8/1974 | Cicione et al. | |
| 4,379,928 A | 4/1983 | Theodoropulos | |
| 4,481,220 A | * | 11/1984 | Giesselmann et al. ........ 514/788 |
| 4,775,673 A | 10/1988 | Koenig et al. | |
| 5,693,126 A | 12/1997 | Ito | |
| 6,136,822 A | 10/2000 | Takagaki et al. | |

FOREIGN PATENT DOCUMENTS

| | | | |
|---|---|---|---|
| CH | 349440 | | 10/1960 |
| CH | 573 702 | | 3/1976 |
| DE | 43 41 986 A1 | | 6/1995 |
| FR | 922 954 | | 6/1947 |
| FR | 2 564 288 A1 | | 11/1985 |
| GB | 579 887 | | 8/1946 |
| JP | 59020258 | * | 2/1984 |
| JP | 2008256991 | * | 10/2008 |
| WO | 2006/003210 A1 | | 1/2006 |
| WO | 2007/107745 A2 | | 9/2007 |
| WO | 2008/101629 A2 | | 8/2008 |
| WO | 2009/027624 A2 | | 3/2009 |
| WO | 2009/027626 A2 | | 3/2009 |

OTHER PUBLICATIONS

Seebach et al, Helv. Chim. Acta, 1977, 60(2), 301-325.*
Written Opinion of the International Searching Authority issued on May 8, 2012, in International Patent Application No. PCT/FR2010/052212.
International Search Report issued on Apr. 5, 2011, by the European Patent Office as the International Searching Authority in International Patent Application No. PCT/FR2010/052212.
Annunziata et al, "Chelation and Non-Chelation Controlled Stereoselective Reduction of α-Methoxy-α-Phenylthio Ketones," Tetrahedron, 1991, pp. 3853-3868, vol. 47, No. 23.
Borowitz et al., "Convenient One-Step Conversions of Alcohols or Phenols to N,N-Dipropyl Alkoxyacetamides," Organic Preparations and Procedures International: The New Journal for Organic Synthesis, 2009, pp. 257-262, vol. 9, No. O.
Chung et al., "Convenient Synthesis of 6-Substituted-2-chloro-5,12-dihydro-5-oxobenzoxazolo[3,2-α]quinolines and N-acylated-3-chlorodibenz[b,e][1,4]oxazepin-11(5H)-ones," Journal of Heterocyclic Chemistry, 1997, pp. 485-488, vol. 34.
Fujita et al., "Fluoride Ion Catalyzed Reduction of Aldehydes and Ketones with Hydrosilanes. Synthetic and Mechanistic Aspects and an Application to the Threo-Directed Reduction of α-Substituted Alkanones," J. Org. Chem., 1988, pp. 5405-5415, vol. 53.
Kobayashi et al., "An Improved Synthetic Method of (S)-2-Alkoxypropanals from Ethyl (S)-Lactate," Bull. Chem. Soc. Jpn., 1989, pp. 3038-3040, vol. 62, No. 9.
Pellissier et al., "Reactions of Isocyanides. II-Addition to Acetals," Tetrahedron Letters, 1986, pp. 3505-3506, vol. 27, No. 30.
Ramírez et al., "Hemilabile Ligands in Organolithium Chemistry: Substituent Effects on Lithium Ion Chelation," J. Am. Chem. Soc., 2003, pp. 41-58 and 15376-15387, vol. 125, No. 50.
Speziale et al., "Synthesis of Cyclopropanetricarboxamides," Journal of Organic Chemistry, 1965, pp. 1199-1202, vol. 30.
Talaty et al., "Regioselectivity in nucleophilic ring-opening of aziridinones," Chem. Commun., 1998, pp. 985-986.
de Voghel et al., "Phosgene Immonium Salts. XIII. Dichloromalonyl Cyanines and 3,5-Bis(dimethylamino)pyrazoles," J. Org. Chem., 1974, pp. 1233-1235, vol. 39, No. 9.
Wright et al., "Analogs of Amphenone. The Synthesis of Aminosubstituted Diphenylacetones and Related Compounds," Journal of the American Chemical Society, 1959, pp. 5193-5199, vol. 81.

* cited by examiner

*Primary Examiner* — Shailendra Kumar
(74) *Attorney, Agent, or Firm* — Dentons US LLP

(57) ABSTRACT

Novel ether-amide compounds are described. Uses of the compounds, in particular as solvents, for example in phytosanitary formulations are also described.

28 Claims, No Drawings

ETHER-AMIDE COMPOUNDS AND USES THEREOF

CROSS-REFERENCE TO PRIORITY/PCT APPLICATIONS

This application is a National Stage of PCT/FR 2010/052212, filed Oct. 18, 2010, and designating the United States (published in the French language on Apr. 28, 2011, as WO 2011/048314 A1; the title and abstract were also published in English), which claims priority of FR 0905000, filed Oct. 19, 2009, each hereby expressly incorporated by reference in its entirety and each assigned to the assignee hereof.

The object of the present invention is novel compounds of the ether amide type. Its object is also the uses of such compounds, notably as solvents, for example in phytosanitary formulations.

The industry uses many chemical compounds as solvents, for example for preparing chemicals and materials, for formulating chemical compounds, or for treating surfaces. For example solvents are used for the formulation of phytosanitary actives notably in the form of emulsifiable concentrates (Emulsifiable Concentrate "EC") intended to be diluted in water by the farmer, before application on a field. Solvents are used for the formulation of phytosanitary actives notably in the form of micro-emulsions ("ME") or emulsions in water (Emulsion in Water "EW") intended to be diluted in water by the farmer before application on a field.

The industry is searching for novel compounds with which it is possible to vary or optimize the products and methods in which solvents, notably polar solvents, are to be used. The industry notably needs compounds with a moderate cost, having interesting properties of use. The industry also needs compounds having a toxicological and/or ecological profile perceived as being favorable, notably low volatility (low VOC), good biodegradability, low toxicity and/or low hazardous nature.

The use of dimethylamides as solvents is known. These are products of formula R-CONMe$_2$ wherein R is a hydrocarbon group such as an alkyl, typically a C$_6$-C$_{30}$ alkyl. Such products are notably marketed under the name of Genagen® by Clariant. These solvents find applications notably in the phytosanitary field. These solvents however have a restricted field of use and do not allow solubilization of certain phytosanitary actives at certain concentrations, in useful temperature ranges, without forming crystals.

Documents WO 2007/107745, WO 2009/027624 and WO 2009/027626 (Syngenta) describe the use of lactamides (alpha-hydroxyamides) as a solvent notably in the phytosanitary field. There exists a need for other solvents.

Document WO 2008/101629 (Cognis) describes the use of lactamides (alpha-hydroxyamides) as a solvent, notably in the phytosanitary field. There exists a need for other solvents.

There also exists a need for plasticizers.

Moreover, document U.S. Pat. No. 3,827,994 (Grace) describes useful compounds in aminoplast resin compositions for treating textiles or papers. The compounds are said to improve properties such as creasing resistance of textiles. The compound of formula CH$_3$—CH(OMe)—CO—NMe$_2$ is notably disclosed in column 26. Other properties or uses are not suggested.

There remains a need for novel solvents, co-solvents, crystallization inhibitors, or plasticizers, notably in phytosanitary formulations, and for novel compounds which may notably widen the range of actives which may be formulated and/or their concentration and/or which may widen their conditions of use, notably in terms of stability for example without forming crystals at low temperature.

The present invention meets at least one of the needs expressed above by proposing the use as a solvent, co-solvent, crystallization inhibitor, or plasticizer, of a compound of the following formula (I):

wherein

R$^a$ and R$^b$, either identical or different, are groups selected from hydrogen and linear or branched, preferably C$_1$-C$_6$, preferably C$_1$-C$_3$ alkyl groups, R$^1$ is a group R$^{'1}$ ou -(AO)$_n$R$^{'1}$, wherein R$^{'1}$ is a group selected from hydrocarbon groups comprising an average number of carbon atoms ranging from 1 to 36, preferably from 1 to 15, either saturated or unsaturated, either linear or branched, optionally cyclic, optionally aromatic, said aromatic groups may comprise a heteroatom in an aromatic ring, AO, either identical or different, represents a group of formula —CH$_2$—CH$_2$—O—, —CHMe-CH$_2$—O—, or —CH$_2$—CHMe-O— n is an average number greater than or equal to 0, ranging for example from 0 to 50, R$^2$ and R$^3$, either identical or different are groups selected from hydrogen and hydrocarbon groups comprising an average number of carbon atoms ranging from 1 to 36, preferably from 1 to 15, either saturated or unsaturated, either linear or branched, optionally cyclic, optionally aromatic, optionally substituted, R$^2$ and R$^3$ may optionally form together a cycle comprising the nitrogen atom to which they are bound, optionally substituted and/or optionally comprising an additional heteroatom, R$^2$ and R$^3$ are not simultaneously hydrogen atoms, with the proviso that if R$^a$=R$^b$=H, the compound of formula (I) is used in a phytosanitary formulation.

The present invention relates to the use as a solvent, co-solvent, crystallization inhibitor, or plasticizer, of a compound of the following formula (I):

wherein

R$^a$ and R$^b$, either identical or different are groups selected from hydrogen and linear or branched, preferably C$_1$-C$_6$, preferably C$_1$-C$_3$ alkyl groups, R$^1$ is a R$^{'1}$ or -(AO)$_n$R$^{'1}$ group, wherein R$^{'1}$ is a group selected from hydrocarbon groups comprising an average number of carbon atoms ranging from 1 to 36, preferably from 1 to 15, either saturated or unsaturated, either linear or branched, optionally cyclic, optionally aromatic, said aromatic groups may comprise a heteroatom in an aromatic ring, AO, either identical or different, represents a group of formula —CH$_2$—CH$_2$—O—, —CHMe-CH$_2$—O—, or —CH$_2$—CHMe-O— n is an average number greater than or equal to 0, ranging for example from 0 to 50, R$^2$ and R$^3$, either identical or different are hydrocarbon groups comprising an average number of carbon atoms ranging from 1 to 36, preferably from 1 to 15, either saturated or unsaturated, either linear or branched, optionally cyclic, optionally aromatic, optionally substituted, R$^2$ and R$^3$ may optionally form together a cycle comprising a nitrogen atom to which they are bound, optionally substituted and/or optionally comprising an additional heteroatom, with the proviso that if $R^a=R^b=H$, the compound of formula (I) is used in a phytosanitary formulation.

The object of the invention is also a method for preparing the compound. The object of the invention is also the use of the compound as a surfactant, solvent, co-solvent, stripping agent, crystallization inhibitor, cleaning agent, degreasing agent, plasticizer or coalescence agent. The object of the invention is also a method for solvatation, co-solvatation, plastification, coalescence and/or crystallization inhibition by adding the compound of the invention. The object of the invention is also formulations comprising the compound of the invention. The formulations may notably be phytosanitary formulations. The object of the present invention is also novel compounds, which may be particularly suitable for uses, for methods or for applying formulations as mentioned above.

Definitions or Abbreviations

In the present application, the following abbreviations are used: Me means methyl, Et means ethyl; IsoAm means Isoamyl, cyclo or Cy means cyclohexyl.

In the present application by "compound of the invention", is meant a compound of formula (I).

In the present application, by "novel compounds of the invention" are meant certain compounds of formula (I).

In the present application, by "material composition" is meant a more or less complex composition comprising several chemical compounds. This may be typically a non-purified or moderately purified reaction product. The compound of the invention may notably be isolated and/or marketed and/or used as a material composition comprising it. The compound of the invention, in the form of a pure molecule or in the form of a mixture fitting formula (I), may be comprised in a material composition.

In the present application the term of solvent is understood in a broad sense, notably covering the functions of co-solvent, crystallization inhibitor, stripping agent. The term of solvent may notably designate a liquid product at the temperature of use, preferably with a melting point of less than or equal to 20° C., preferably 5° C., preferably 0° C., which may contribute to liquefying a solid material, or to preventing or delaying solidification or crystallization of material in a liquid medium.

In the present application, the expression "hydrocarbon groups" notably designates saturated or unsaturated, linear or branched acyclic aliphatic groups, or saturated, unsaturated or aromatic, monocyclic or polycyclic, carbocyclic or heterocyclic groups, or further linkings of said groups.

Compound of the Invention

The compound of the invention has the general formula (I) given above. It is noted that this may be a mixture of several compounds of general formula (I). In other words, the compound may be alone or as a mixture. Within the scope of mixtures of several compounds, the numbers of atoms or units may be expressed as average numbers. These are number average numbers. In the case of single compounds, they will generally be integers, as regards the number of carbon atoms.

The groups $R^a$ and $R^b$, either identical or different are groups selected from hydrogen and linear or branched alkyl groups. The alkyls may notably be $C_1$-$C_6$, preferably $C_1$-$C_4$ and preferentially $C_1$-$C_3$ alkyls. These may notably be methyl, ethyl, propyl or butyl groups. According to a particular embodiment, the total number of carbon atoms (in the compound of formula (I)) excluding the groups $R^1$, $R^2$ and $R^3$, is 2, 3, 4, 5, 6, 7 or 8, or average numbers between each of these values.

It is mentioned that according to a particular embodiment, at least one of the groups selected from $R^a$ and $R^b$ is different from hydrogen, for example a group selected from linear or branched alky groups. The alkyls may notably be $C_1$-$C_6$, preferably $C_1$-$C_4$ and preferentially $C_1$-$C_3$ alkyls. These may notably be methyl, ethyl, propyl or butyl groups. According to a particular embodiment, the total number of carbon atoms excluding the groups $R^1$, $R^2$ and $R^3$ is 2, 3, 4, 5, 6, 7, or 8 or average numbers between each of these values. For example $R^a$=Me or Et, and $R^b$=H.

It is mentioned that $R^2$ may be a group selected from linear or branched alkyl groups, the alkyls may notably be $C_1$-$C_6$, preferably $C_1$-$C_4$ and preferentially $C_1$-$C_3$ alkyls. These may notably be methyl, ethyl, propyl or butyl groups. According to a particular embodiment, the total number of carbon atoms, excluding the groups $R^1$, $R^2$ and $R^3$ is 3, 4, 5, 6, 7 or 8 or average numbers between each of these values.

It is mentioned that $R^b$ may be a group selected from hydrogen and linear or branched alkyl groups. The alkyls may notably be $C_1$-$C_6$, preferably $C_1$-$C_4$ and preferentially $C_1$-$C_3$ alkyls. These may notably be methyl, ethyl, propyl or butyl groups. According to a particular embodiment, the total number of carbon atoms, excluding the groups $R^1$, $R^2$ and $R^3$ is 2, 3, 4, 5, 6, 7 or 8 or average numbers between each of these values. $R^b$ is preferably a hydrogen.

According to a particular embodiment:

$R^a$ is a group selected from linear or branched alkyl groups. The alkyls may notably be $C_1$-$C_6$, preferably $C_1$-$C_3$ alkyls. These may notably be methyl or ethyl groups. According to a particular embodiment, the total number of carbon atoms, excluding the groups $R^1$, $R^2$ and $R^3$ is 3, 4, 5, 6, 7, or 8.

$R^b$ is a group selected from hydrogen and linear or branched alkyl groups. The alkyls may notably be $C_1$-$C_6$, preferably $C_1$-$C_3$ alkyls. These may notably be methyl or ethyl groups. According to a particular embodiment, the total number of carbon atoms, excluding the groups $R^1$, $R^2$ and $R^3$ is 3, 4, 5, 6, 7, or 8. $R^b$ is preferably a hydrogen.

The embodiment wherein $R^a$=Me, and $R^b$=H, may correspond to compounds derived from lactic acid of formula $CH_3$—CHOH—COOH with an ether —$OR^1$ in the place of the hydroxyl and an amide —$CONR^2R^3$ in the place of the acid —COOH.

According to a particular embodiment, the compounds of formula (I) are characterized in that $R^a$ is a linear or branched $C_1$-$C_6$ alkyl group, and $R^b$ is H or a linear or branched $C_1$-$C_6$ alkyl group. Such compounds are also called 'branched compounds'.

The present invention therefore according to an advantageous embodiment relates to the use as a solvent, co-solvent, crystallization inhibitor, or plasticizer, of a compound of the following formula (I):

$$R^aR^bC(OR^1)—CONR^2R^3 \quad (I)$$

wherein $R^a$ is a linear or branched $C_1$-$C_6$ alkyl group, $R^b$ is H or a linear or branched $C_1$-$C_6$ alkyl group, $R^1$ is a group $R^{11}$ or -$(AO)_nR^{11}$, wherein $R^{11}$ is a group selected from hydrocarbon groups comprising an average number of carbon atoms ranging from 1 to 15, optionally substituted, selected from the saturated or unsaturated, linear or branched acyclic aliphatic groups, saturated, unsaturated or aromatic, monocyclic or polycyclic, carbocyclic or heterocyclic groups, and the linkings of said groups, AO, either identical or different, represents a group of formula —$CH_2$—$CH_2$—O—, —CHMe-$CH_2$—O—, or —$CH_2$—CHMe-O— n is an average number greater than or equal to 0, ranging for example from 0 to 50, $R^2$ and $R^3$, either identical or different are hydrocarbon groups comprising an average number of carbon atoms ranging from 1 to 15, optionally substituted, selected from saturated or unsaturated, linear or branched acyclic aliphatic groups, saturated, unsaturated or aromatic, monocyclic or polycyclic, carbocyclic or heterocyclic groups and the linkings of said groups, $R^2$ and $R^3$ may optionally form together a cycle comprising the nitrogen atom to which they are bound, optionally substituted and/or optionally comprising an additional heteroatom.

According to a particular embodiment, "G" for the compound of the invention, $R^a$=Me, $R^b$=H and $R^1$ is a group different from the methyl group. All the following in this paragraph relates to this particular embodiment "G". According to a particular embodiment, $R^a$=Me, $R^b$=H and $R^1$ is a group different from n-butyl. According to a particular embodiment $R^a$=Me, $R^b$=H and $R^1$ is an alkyl group comprising from 2 to 5 carbon atoms, excluding n-butyl, for example an ethyl, n-propyl, isopropyl, isobutyl, tertbutyl, n-pentyl, isopentyl, isoamyl group. According to a particular embodiment $R^a$=Me, $R^b$=H and $R^1$ is a cyclic group preferably a cyclohexyl group. According to a particular embodiment, $R^1$ is a group different from a methyl group. According to a particular embodiment, $R^1$ is a group different from n-butyl. According to a particular embodiment $R^1$ is a cyclic group, preferably a cyclohexyl group. According to a particular embodiment $R^1$ is an alkyl group comprising from 2 to 5 carbon atoms, excluding n-butyl, for example an ethyl, n-propyl, isopropyl, isobutyl, tertbutyl, n-pentyl, isopentyl, isoamyl group. According to a particular embodiment $R^a$=Me, $R^b$=H and if $R^1$ is an alkyl group, it then comprises more than 5 carbon atoms, $R^1$ may for example be an n-hexyl, cyclohexyl, n-octyl, isooctyl, 2-ethylhexyl, decyl, dodecyl, tridecyl, phenyl or benzyl group. According to a particular embodiment $R^a$=Me, $R^b$=H and $R^1$ is an alkyl group comprising more than 5 carbon atoms. It is mentioned that according to another particular embodiment $R^a$=$R^b$=H.

This embodiment may correspond to compounds derived from glycolic acid of formula $CH_2OH$—$COOH$ with an ether —$OR^1$ in the place of the hydroxyl and an amide —$ONR^2R^3$ in the place of the acid —COOH.

According to an embodiment, the compounds of formula (I) are characterized in that $R^a$ and $R^b$ are H. Such compounds are also called 'linear compounds'.

Thus, according to a particular embodiment, the present invention relates to the use as a solvent, co-solvent, crystallization inhibitor, or plasticizer, in a phytosanitary formulation, of a compound of the following formula (I-1):

(I-1)

wherein
$R^1$ is a group $R^{t1}$ or -$(AO)_nR^{t1}$, wherein
$R^{t1}$ is a group selected from hydrocarbon groups comprising an average number of carbon atoms ranging from 1 to 15, optionally substituted, selected from saturated or unsaturated, linear or branched acyclic aliphatic groups, saturated, unsaturated or aromatic, monocyclic or polycyclic, carbocyclic or heterocyclic groups, and the linkings of said groups,
AO, either identical or different, represents a group of formula —$CH_2$—$CH_2$—O—, —CHMe-$CH_2$—O—, or —$CH_2$—CHMe-O—
n is an average number greater than or equal to 0,
$R^2$ and $R^3$, either identical or different, are hydrocarbon groups comprising an average number of carbon atoms ranging from 1 to 15, optionally substituted, selected from saturated or unsaturated, linear or branched acyclic aliphatic groups, saturated, unsaturated or aromatic, monocyclic or polycyclic, carbocyclic or heterocyclic groups and the linkings of said groups, $R^2$ and $R^3$ may optionally form together a cycle comprising the nitrogen atom to which they are bound optionally substituted and/or optionally comprising an additional heteroatom.

According to a particular embodiment $R^a$=$R^b$=H and $R^1$ is a cyclic group, preferably a cyclohexyl group. The compounds having such a group have particularly interesting solvating properties and/or miscibility properties in water, notably within the scope of phytosanitary formulations.

According to a particular embodiment "I" for the compound of the invention, $R^a$=$R^b$=H and $R^1$ is a group different from the methyl group. All the following in this paragraph relates to this particular embodiment "I". According to a particular embodiment $R^a$=$R^b$=H and $R^1$ is a group different from n-butyl. According to a particular embodiment $R^a$=$R^b$=H and $R^1$ is an alkyl group comprising from 2 to 8 carbon atoms, excluding n-butyl, for example an ethyl, n-propyl, isopropyl, isobutyl, tertbutyl, n-pentyl, isopentyl, isoamyl, n-hexyl, cyclohexyl, n-octyl, isooctyl, 2-ethylhexyl group. According to a particular embodiment $R^a$=$R^b$=H and $R^1$ is a cyclic group, preferably a cyclohexyl group. According to a particular embodiment, $R^1$ is a group different from the methyl group. According to a particular embodiment, $R^1$ is a group different from n-butyl. According to a particular embodiment, $R^1$ is a cyclic group, preferably a cyclohexyl group. According to a particular embodiment, $R^1$ is an alkyl group comprising from 2 to 8 carbon atoms, excluding n-butyl, for example an ethyl, n-propyl, isopropyl, isobutyl, tertbutyl, n-pentyl, isopentyl, isoamyl, n-hexyl, cyclohexyl, n-octyl, isooctyl, 2-ethylhexyl group. According to a particular embodiment $R^a$=$R^b$=H and if $R^1$ is an alkyl group it then comprises more than 8 carbon atoms, $R^1$ may for example be a decyl, dodecyl, tridecyl, phenyl or benzyl group. According to a particular embodiment $R^a$=$R^b$=H and $R^1$ is an alkyl group, comprising more than 8 carbon atoms.

In formula (I), the groups $R^2$ and $R^3$, either identical or different are groups selected from hydrogen and hydrocarbon groups comprising an average number of carbon atoms ranging from 1 to 36, either saturated or unsaturated, either linear or branched, optionally cyclic, optionally aromatic, optionally substituted, $R^2$ and $R^3$ may optionally form together a cycle comprising the nitrogen atom to which they are bound, optionally substituted and/or optionally comprising an additional heteroatom. It should be noted that $R^2$ and $R^3$ are not simultaneously hydrogens. In other words, the group —$CONR^2R^3$ is not a group —$CONH_2$. This may be a group —$CONHR^2$ wherein $R^2$ is not a hydrogen, or a group —$CONR^2R^3$ wherein $R^2$ and $R^3$ are not hydrogens. $R^2$ and $R^3$, either identical or different, may for example be selected from methyl, ethyl, propyl (n-propyl), isopropyl, n-butyl, isobutyl, n-pentyl, amyl, isoamyl, hexyl, cyclohexyl groups, mixtures and/or combinations thereof. $R^2$ and $R^3$ may also be such that they form together with the nitrogen atom, a morpholine pyrrolidine, piperazine or piperidine group. $R^2$ and $R^3$ may notably be ethyl groups, preferably both of them.

The group $R^1$ is a group typically corresponding to an alcohol $R^1$—OH. In one case, it may correspond to a simple alcohol $R^{t1}$—OH. In another case, it may correspond to an ethoxylated and/or propoxylated alcohol of formula HO-$(AO)_n R^{r1}$. $R^{r1}$ represents the hydrocarbon radical of these optionally ethoxylated and/or propoxylated alcohols. The group $R^{r1}$ is a group selected from hydrocarbon groups comprising an average number of carbon atoms ranging from 1 to 36, either saturated or unsaturated, either linear or branched, optionally cyclic, optionally aromatic, said aromatic groups may comprise a heteroatom in an aromatic ring. The heteroatom of the aromatic group may be an oxygen or nitrogen atom. It is mentioned that the aromatic group may be directly bound through or borne by an alkyl group. It is mentioned that the cyclic or aromatic groups may be substituted. $R^{r1}$ may for example be selected from methyl, ethyl, propyl, isopropyl, n-butyl, isobutyl, n-pentyl, isopentyl, isoamyl, n-hexyl, cyclohexyl, n-octyl, isooctyl, 2-ethylhexyl, decyl, dodecyl, tridecyl, phenyl, benzyl groups and mixtures thereof. It is noted that $R^{r1}$ may be a more or less complex mixture, which may correspond to the application of a more or less complex mixture of alcohols $R^1$—OH, for example fusel oil.

According to a particular embodiment, the group $R^1$ is a cyclic group, preferably a cyclohexyl group.

The group (AO) represents an ethoxy group of formula —$CH_2$—$CH_2$—O— or a propoxy group of formula —CHMe-$CH_2$—O—, or —$CH_2$—CHMe-O—. The number n is an average number greater than or equal to 0, for example ranging from 0 to 50. It typically represents a degree of ethoxylation and/or propoxylation. In the case when ethoxy and propoxy groups are present, they may be distributed randomly or in a sequenced way.

The compound of the invention is preferably such that it has a melting point of less than or equal to 20° C., preferably 5° C., preferably 0° C. The groups detailed above are preferably such that the compound has this property.

According to an embodiment, the compound of the invention may be totally miscible in water. According to a particular embodiment, the compound of the invention is partly miscible in water. The miscibility in water may for example be less than 10% by weight (at 25° C.), preferably 2%, preferably 1% or 0.1%. It may be greater than 0.001%, preferably 0.01% or 0.1%. For example, it may be comprised between 0.01% and 2%, for example between 0.1% and 1%. Surprisingly, the compounds of the invention have good solvating properties, notably for phytosanitary actives in phytosanitary formulations with low miscibility in water. The groups $R^a$, $R^b$, and/or the group $R^1$ and/or the groups $R^2$, $R^3$ may be selected so as to control the miscibility in water.

The compound of the invention may notably have one of the following formulae:

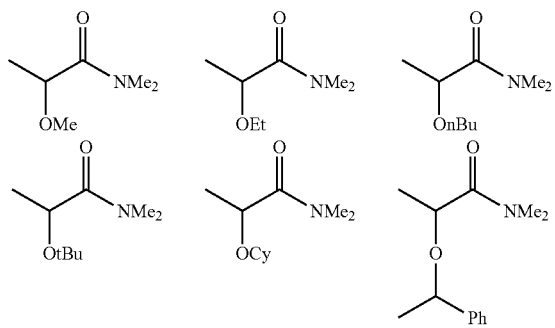

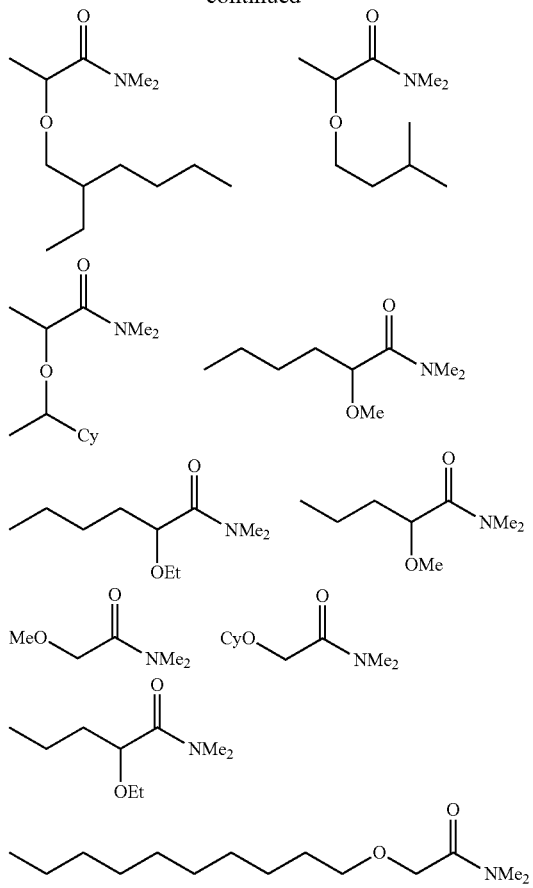

The compound of the invention may notably be one of the novel compounds of the invention, detailed below.

It is mentioned that the compound of the invention may be comprised in a material composition, comprising products other than the compound alone or as a mixture fitting formula (I). In the material composition, the compound of the invention may account for at least 10% by weight. Preferably, this is the main compound of the material composition. By main compound in the present application is meant the compound for which the content is the highest, even if its content is less than 50% by weight (for example in a mixture of 40% of A, 30% of B, and 30% of C, product A is the main compound). Even more preferably, the compound of the invention accounts for at least 50% by weight of the material composition, for example from 70 to 95% by weight, and even from 75 to 90% by weight. As indicated above, the material composition may be a reaction product. The other products of the material composition may notably be byproducts of impurities, of unreacted products, or products corresponding to reaction adducts of products comprised in the initial compounds not leading to the compounds of formula (I).

Novel Compounds of the Invention

The invention also relates to certain novel compounds of formula (I). These particular novel compounds may be applied as compounds of the invention.

The novel compounds are the following compounds of formula (I):

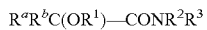     (I)

wherein
R$^a$, R$^b$, either identical or different, are groups selected from hydrogen and linear or branched, preferably C$_1$-C$_3$ alkyl groups,
R$^1$ is a group R$^{1'}$ or -(AO)$_n$R$^{1'}$, wherein
R$^{1'}$ is a group selected form hydrocarbon groups comprising an average number of carbon atoms ranging from 1 to 36, either saturated or unsaturated, either linear or branched, optionally cyclic, optionally aromatic, said aromatic groups may comprise a heteroatom in an aromatic ring,
AO, either identical or different, represents a group of formula —CH$_2$—CH$_2$—O—, —CHMe-CH$_2$—O—, or —CH$_2$—CHMe-O—
n is an average number greater than or equal to 0, ranging for example from 0 to 50,
R$^2$ and R$^3$, either identical or different, are groups selected from hydrogen and hydrocarbon groups comprising an average number of carbon atoms ranging from 1 to 36, either saturated or unsaturated, either linear or branched, optionally cyclic, optionally aromatic, optionally substituted, R$^2$ and R$^3$ may optionally form together a cycle comprising the nitrogen atom to which they are bound, optionally substituted and/or optionally comprising an additional heteroatom,
R$^2$ and R$^3$ are not hydrogens simultaneously,
with the following conditions:
if R$^a$=R$^b$=H, then R$^1$ is a group different from methyl or n-butyl groups,
if R$^a$=Me and R$^b$=H, then R$^1$ is a group different from methyl or n-butyl groups.
Preferably, R$^1$ is a group different from methyl or n-butyl groups in every case.
What was indicated for the groups R$^a$, R$^b$ and R$^1$ of the compounds of the invention may be applied to the novel compounds, to the extent that the above conditions are observed.
According to a particular embodiment, the present invention relates to novel branched compounds.
Thus, the present invention relates to compounds of the following formula (I):

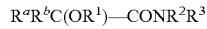

R$^a$R$^b$C(OR$^1$)—CONR$^2$R$^3$ (I)

wherein
R$^a$ is a linear or branched C$_1$-C$_6$ alkyl group,
R$^b$ is H or a linear or branched C$_1$-C$_6$ alkyl group
R$^1$ is a group R$^{1'}$ or -(AO)$_n$R$^1$, wherein
R$^{1'}$ is a group selected from hydrocarbon groups comprising an average number of carbon atoms ranging from 1 to 15, optionally substituted, selected from either saturated or unsaturated, linear or branched acyclic aliphatic groups, saturated, unsaturated or aromatic, monocyclic or polycyclic, carbocyclic or heterocyclic groups, and the linkings of said groups,
AO, either identical or different, represents a group of formula —CH$_2$—CH$_2$—O—, —CHMe-CH$_2$—O—, or —CH$_2$—CHMe-O—
n is an average number greater than or equal to 0,
R$^2$ and R$^3$, either identical or different, are hydrocarbon groups comprising an average number of carbon atoms ranging from 1 to 15, optionally substituted, selected from saturated or unsaturated, linear or branched acyclic or aliphatic groups, saturated, unsaturated or aromatic monocyclic or polycyclic, carbocyclic or heterocyclic groups and the linkings of said groups,
R$^2$ and R$^3$ may optionally form together a cycle comprising the nitrogen atom to which they are bound, optionally substituted and/or optionally comprising an additional heteroatom, and
with the following conditions:
if R$^a$=Me and R$^b$=H, then R$^1$ is a group different from methyl, n-butyl, benzyl or t-butyl groups,
Notably, according to a particular embodiment "G" for the compound of the invention, R$^a$=Me, R$^b$=H and R$^1$ is a group different from a methyl group. All the following in this paragraph relates to this particular embodiment "G". According to a particular embodiment, R$^a$=Me, R$^b$=H and R$^1$ is a group different from n-butyl. According to a particular embodiment R$^a$=Me, R$^b$=H and R$^1$ is a group different from t-butyl or benzyl. According to a particular embodiment R$^a$=Me, R$^b$=H and R$^1$ is an alkyl group comprising from 2 to 5 carbon atoms, excluding n-butyl or t-butyl, for example an ethyl, n-propyl, isopropyl, isobutyl, n-pentyl, isopentyl, isoamyl group. According to a particular embodiment R$^a$=Me, R$^b$=H and R$^1$ is a cyclic group, preferably a cyclohexyl group. According to a particular embodiment R$^1$ is a group different from a methyl group According to a particular embodiment, R$^1$ is a group different from n-butyl. According to a particular embodiment, R$^1$ is a cyclic group, preferably a cyclohexyl group. According to a particular embodiment, R$^1$ is an alkyl group comprising from 2 to 5 carbon atoms, excluding n-butyl, for example an ethyl, n-propyl, isopropyl, isobutyl, tertbutyl, n-pentyl, isopentyl, isoamyl group. According to a particular embodiment R$^a$=Me, R$^b$=H and if R$^1$ is an alkyl group, it then comprises more than 5 carbon atoms, R$^1$ may for example be a n-hexyl, cyclohexyl, n-octyl, isooctyl, 2-ethylhexyl, decyl, dodecyl, tridecyl or phenyl group. According to a particular embodiment R$^a$=Me, R$^b$=H and R$^1$ is an alkyl group, comprising more than 5 carbon atoms. According to a particular embodiment, R$^1$ is an alkyl group comprising from 2 to 5 carbon atoms, excluding t-butyl or n-butyl, for example an ethyl, n-propyl, isopropyl, isobutyl, n-pentyl, isopentyl, or isoamyl group.

According to a particular embodiment, R$^1$ is an alkyl group comprising from 3 to 5 carbon atoms, excluding t-butyl or n-butyl, for example an n-propyl, isopropyl, isobutyl, n-pentyl, isopentyl, or isoamyl group.

Among the preferred branched compounds, R$^1$ is a linear or branched alkyl group comprising more than 5 carbon atoms.

More particularly, the preferred branched compounds according to the present invention are characterized in that R$^2$ is a linear or branched C$_1$-C$_3$ alkyl group and in that R$^b$ is H or a linear or branched C$_1$-C$_3$ alkyl group.

The preferred branched compounds are compounds of formula (I) as defined above, wherein:
R$^a$=Me, Et, n-Pr or n-Bu, and
R$^b$=H.

According to a more preferred embodiment, the branched compounds of the invention are characterized in that R$^2$ and R$^3$ are methyl groups.

Preferably, in formula (I) of the novel branched compounds according to the present invention, R$^{1'}$ is selected from ethyl, propyl, isopropyl, n-pentyl, isopentyl, isoamyl, n-hexyl, cyclohexyl, n-octyl, isooctyl, 2-ethylhexyl, decyl, dodecyl, tridecyl and 1-phenylethyl groups.

A preferred family of novel branched compounds according to the present invention consists of compounds of formula (I) as defined above wherein R$^1$ is a methyl or ethyl group.

Among the preferred branched compounds, mention may be made of the compounds of formula (I) as defined above wherein R$^2$ is an alkyl group comprising 2, 3 or 4 carbon atoms.

Another family of branched compounds according to the present invention consists of compounds of formula (I) as defined above wherein $R^a$ is an alkyl group comprising 2, 3 or 4 carbon atoms and $R^2$ and $R^3$ are methyl groups.

Another family of branched compounds according to the present invention consists of compounds of formula (I) as defined above wherein $R^a$ is an alkyl group comprising 2, 3 or 4 carbon atoms and $R^1$ is a methyl or ethyl group. Preferably, for these preferred compounds, $R^2$ and $R^3$ are methyl groups.

A preferred family of the novel branched compounds according to the present invention consists of compounds of formula (I) as defined above wherein $R^1$ is a branched alkyl group other than a t-butyl group, optionally substituted with a phenyl group.

A preferred family of the novel branched compounds according to the present invention consists of compounds of formula (I) as defined above wherein $R^1$ is a cycloalkyl group.

Among the preferred branched compounds, mention may notably be made of the following compounds:

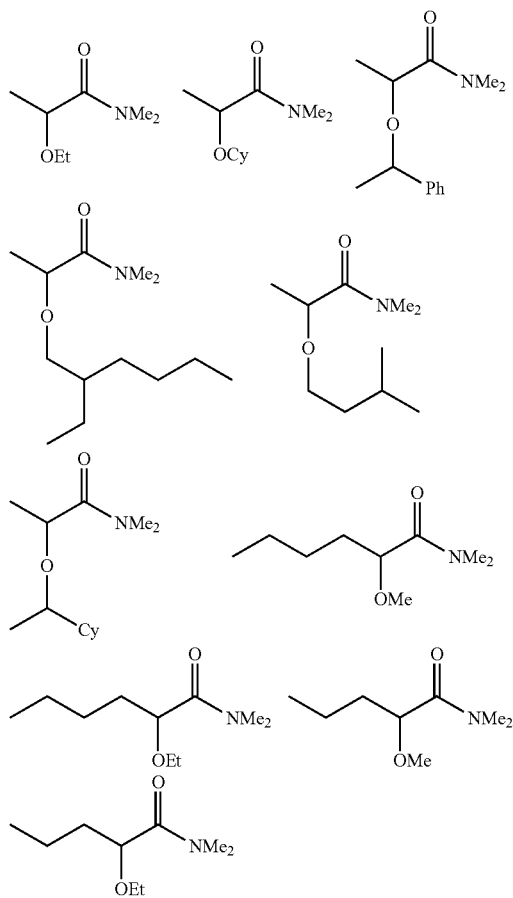

According to another particular embodiment, the present invention relates to novel linear compounds.

Thus the present invention also relates to compounds of the following formula (I-1):

wherein
$R^1$ is a $R^{1'}$ or $-(AO)_n R^{1'}$ group, wherein
$R^{1'}$ is a group selected from hydrocarbon groups comprising an average number of carbon atoms ranging from 1 to 15, optionally substituted, selected from saturated or unsaturated, linear or branched acyclic aliphatic groups, saturated, unsaturated or aromatic, monocyclic or polycyclic, carbocyclic or heterocyclic groups and the linkings of said groups, AO, either identical or different, represents a group of formula $-CH_2-CH_2-O-$, $-CHMe-CH_2-O-$, or $-CH_2-CHMe-O-$ n is an average number greater than or equal to 0, for example ranging from 0 to 50, $R^2$ and $R^3$, either identical or different, are hydrocarbon groups comprising an average number of carbon atoms ranging from 1 to 15, optionally substituted, selected from saturated or unsaturated, linear or branched acyclic aliphatic groups, saturated, unsaturated or aromatic, monocyclic or polycyclic, carbocyclic or heterocyclic groups and the linkings of said groups, with the following conditions:

$R^1$ is a group different from methyl, phenyl, or n-butyl groups.

Notably according to a particular embodiment "I" for the compound of the invention, $R^a=R^b=H$ and $R^1$ is a group different from a methyl group. All the following in this paragraph relates to this particular embodiment "I". According to a particular embodiment, $R^a=R^b=H$ and $R^1$ is a group different from n-butyl. According to a particular embodiment $R^a=R^b=H$ and $R^1$ is a group different from phenyl. According to a particular embodiment, $R^a=R^b=H$ and $R^1$ is an alkyl group comprising from 2 to 8 carbon atoms, excluding n-butyl, for example an ethyl n-propyl, isopropyl, isobutyl, tert-butyl, n-pentyl, isopentyl, isoamyl, n-hexyl, cyclohexyl, n-octyl, isooctyl, 2-ethylhexyl group. According to a particular embodiment, $R^a=R^b=H$ and $R^1$ is a cyclic group, preferably a cyclohexyl group. According to a particular embodiment, $R^1$ is a group different from a methyl group. According to a particular embodiment, $R^1$ is a group different from n-butyl. According to a particular embodiment, $R^1$ is a cyclic group, preferably a cyclohexyl group. According to a particular embodiment, $R^1$ is an alkyl group comprising from 2 to 8 carbon atoms, excluding n-butyl, for example an ethyl, n-propyl, isopropyl, isobutyl, tertbutyl, n-pentyl, isopentyl, isoamyl, n-hexyl, cyclohexyl, n-octyl, isooctyl, 2-ethylhexyl group. According to a particular embodiment, $R^a=R^b=H$ and if $R^1$ is an alkyl group, it then comprises more than 8 carbon atoms, $R^1$ may for example be a decyl, dodecyl, tridecyl, or benzyl group. According to a particular embodiment $R^a=R^b=H$ and $R^1$ is an alkyl group, comprising more than 8 carbon atoms.

A particular family of linear compounds according to the present invention consists of compounds of formula (I-1) as defined above wherein $R^2$ and $R^3$ are methyl groups.

Preferably, in the formula (I-1) as defined above $R^{1'}$ is selected from ethyl, propyl, isopropyl, n-pentyl, isopentyl, isoamyl, n-hexyl, cyclohexyl, n-octyl, isooctyl, 2-ethylhexyl, decyl, dodecyl, tridecyl and 1-phenylethyl groups.

A particular family of linear compounds according to the present invention consists of compounds of formula (I-1) as defined above wherein $R^1$ is a cyclohexyl or n-decyl group.

Another preferred family of linear compounds according to the present invention consists of compounds of formula (I-1) as defined above wherein $R^1$ is a cycloalkyl group, $R^2$ and $R^3$ preferably being methyl groups.

Another preferred family of linear compounds according to the present invention consists of compounds of formula (I-1) as defined above wherein $R^1$ is an alkyl group comprising at least 8 carbon atoms, and notably 10 carbon atoms.

Another preferred family of linear compounds according to the present invention consists of compounds of formula (I-1) as defined above wherein $R^1$ is an alkyl group comprising at least 8 carbon atoms, and $R^2$ and $R^3$ are methyl groups.

Among the preferred linear compounds, mention may notably be made of the following compounds:

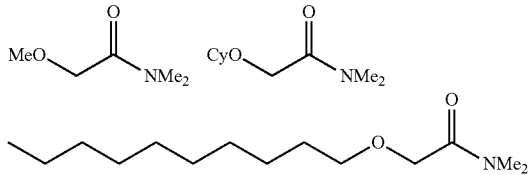

Examples of novel compounds of the invention are the following:

$CH_3$—CH(O-Et)-$CONMe_2$
$CH_3$—CH(O-n-propyl)-$CONMe_2$
$CH_3$—CH(O-isopropyl)-$CONMe_2$
$CH_3$—CH(O-isobutyl)-$CONMe_2$
$CH_3$—CH(O-n-pentyl)-$CONMe_2$
$CH_3$—CH(O-isopentyl)-$CONMe_2$
$CH_3$—CH(O-isoamyl)-$CONMe_2$
$CH_3$—CH(O-n-hexyl)-$CONMe_2$
$CH_3$—CH(O-cyclohexyl)-$CONMe_2$
$CH_3$—CH(O-n-octyl)-$CONMe_2$
$CH_3$—CH(O-isooctyl)-$CONMe_2$
$CH_3$—CH(O-2-ethylhexyl)-$CONMe_2$
$CH_3$—CH(O-decyl)-$CONMe_2$
$CH_3$—CH(O-dodecyl)-$CONMe_2$
$CH_3$—CH(O-phenyl)-$CONMe_2$
$CH_2$(O-Et)-$CONMe_2$
$CH_2$(O-n-propyl)-$CONMe_2$
$CH_2$(O-isopropyl)-$CONMe_2$
$CH_2$(O-isobutyl)-$CONMe_2$
$CH_2$(O-tertbutyl)-$CONMe_2$
$CH_2$(O-n-pentyl)-$CONMe_2$
$CH_2$(O-isopentyl)-$CONMe_2$
$CH_2$(O-isoamyl)-$CONMe_2$
$CH_2$(O-n-hexyl)-$CONMe_2$
$CH_2$(O-cyclohexyl)-$CONMe_2$
$CH_2$(O-n-octyl)-$CONMe_2$
$CH_2$(O-isooctyl)-$CONMe_2$
$CH_2$(O-2-ethylhexyl)-$CONMe_2$
$CH_2$(O-decyl)-$CONMe_2$
$CH_2$(O-dodecyl)-$CONMe_2$
$CH_2$(O-benzyl)-$CONMe_2$
$(CH_3)_2$C(O-Me)-$CONMe_2$
$(CH_3)_2$C(O-Et)-$CONMe_2$
$(CH_3)_2$C(O-n-propyl)-$CONMe_2$
$(CH_3)_2$C(O-isopropyl)-$CONMe_2$
$(CH_3)_2$C(O-n-butyl)-$CONMe_2$
$(CH_3)_2$C(O-isobutyl)-$CONMe_2$
$(CH_3)_2$C(O-tertbutyl)-$CONMe_2$
$(CH_3)_2$C(O-n-pentyl)-$CONMe_2$
$(CH_3)_2$C(O-isopentyl)-$CONMe_2$
$(CH_3)_2$C(O-isoamyl)-$CONMe_2$
$(CH_3)_2$C(O-n-hexyl)-$CONMe_2$
$(CH_3)_2$C(O-cyclohexyl)-$CONMe_2$
$(CH_3)_2$C(O-n-octyl)-$CONMe_2$
$(CH_3)_2$C(O-isooctyl)-$CONMe_2$
$(CH_3)_2$C(O-2-ethylhexyl)-$CONMe_2$
$(CH_3)_2$C(O-decyl)-$CONMe_2$
$(CH_3)_2$C(O-dodecyl)-$CONMe_2$
$(CH_3)_2$C(O-phenyl)-$CONMe_2$
$(CH_3)_2$C(O-benzyl)-$CONMe_2$
$CH_3$—$CH_2$—CH(O-Me)-$CONMe_2$
$CH_3$—$CH_2$—CH(O-Et)-$CONMe_2$
$CH_3$—$CH_2$—CH(O-n-propyl)-$CONMe_2$
$CH_3$—$CH_2$—CH(O-isopropyl)-$CONMe_2$
$CH_3$—$CH_2$—CH(O-n-butyl)-$CONMe_2$
$CH_3$—$CH_2$—CH(O-isobutyl)-$CONMe_2$
$CH_3$—$CH_2$—CH(O-tertbutyl)-$CONMe_2$
$CH_3$—$CH_2$—CH(O-n-pentyl)-$CONMe_2$
$CH_3$—$CH_2$—CH(O-isopentyl)-$CONMe_2$
$CH_3$—$CH_2$—CH(O-isoamyl)-$CONMe_2$
$CH_3$—$CH_2$—CH(O-n-hexyl)-$CONMe_2$
$CH_3$—$CH_2$—CH(O-cyclohexyl)-$CONMe_2$
$CH_3$—$CH_2$—CH(O-n-octyl)-$CONMe_2$
$CH_3$—$CH_2$—CH(O-isooctyl)-$CONMe_2$
$CH_3$—$CH_2$—CH(O-2ethylhexyl)-$CONMe_2$
$CH_3$—$CH_2$—CH(O-decyl)-$CONMe_2$
$CH_3$—$CH_2$—CH(O-dodecyl)-$CONMe_2$
$CH_3$—$CH_2$—CH(O-phenyl)-$CONMe_2$
$CH_3$—$CH_2$—CH(O-benzyl)-$CONMe_2$
$CH_3$—$CH_2$—CMe(O-Me)-$CONMe_2$
$CH_3$—$CH_2$—CMe(O-Et)-$CONMe_2$
$CH_3$—$CH_2$—CMe(O-n-propyl)-$CONMe_2$
$CH_3$—$CH_2$—CMe(O-isopropyl)-$CONMe_2$
$CH_3$—$CH_2$—CMe(O-n-butyl)-$CONMe_2$
$CH_3$—$CH_2$—CMe(O-isobutyl)-$CONMe_2$
$CH_3$—$CH_2$—CMe(O-tertbutyl)-$CONMe_2$
$CH_3$—$CH_2$—CMe(O-n-pentyl)-$CONMe_2$
$CH_3$—$CH_2$—CMe(O-isopentyl)-$CONMe_2$
$CH_3$—$CH_2$—CMe(O-isoamyl)-$CONMe_2$
$CH_3$—$CH_2$—CMe(O-n-hexyl)-$CONMe_2$
$CH_3$—$CH_2$—CMe(O-cyclohexyl)-$CONMe_2$
$CH_3$—$CH_2$—CMe(O-n-octyl)-$CONMe_2$
$CH_3$—$CH_2$—CMe(O-isooctyl)-$CONMe_2$
$CH_3$—$CH_2$—CMe(O-2-ethylhexyl)-$CONMe_2$
$CH_3$—$CH_2$—CMe(O-decyl)-$CONMe_2$
$CH_3$—$CH_2$—CMe(O-dodecyl)-$CONMe_2$
$CH_3$—$CH_2$—CMe(O-phenyl)-$CONMe_2$
$CH_3$—$CH_2$—CMe(O-benzyl)-$CONMe_2$
$(CH_3$—$CH_2)_2$C(O-Me)-$CONMe_2$
$(CH_3$—$CH_2)_2$C(O-Et)-$CONMe_2$
$(CH_3$—$CH_2)_2$C(O-n-propyl)-$CONMe_2$
$(CH_3$—$CH_2)_2$C(O-isopropyl)-$CONMe_2$
$(CH_3$—$CH_2)_2$C(O-n-butyl)-$CONMe_2$
$(CH_3$—$CH_2)_2$C(O-isobutyl)-$CONMe_2$
$(CH_3$—$CH_2)_2$C(O-tertbutyl)-$CONMe_2$
$(CH_3$—$CH_2)_2$C(O-n-pentyl)-$CONMe_2$
$(CH_3$—$CH_2)_2$C(O-isopentyl)-$CONMe_2$
$(CH_3$—$CH_2)_2$C(O-isoamyl)-$CONMe_2$
$(CH_3$—$CH_2)_2$C(O-n-hexyl)-$CONMe_2$
$(CH_3$—$CH_2)_2$C(O-cyclohexyl)-$CONMe_2$
$(CH_3$—$CH_2)_2$C(O-n-octyl)-$CONMe_2$
$(CH_3$—$CH_2)_2$C(O-isooctyl)-$CONMe_2$
$(CH_3$—$CH_2)_2$C(O-2-ethylhexyl)-$CONMe_2$
$(CH_3$—$CH_2)_2$C(O-decyl)-$CONMe_2$
$(CH_3$—$CH_2)_2$C(O-dodecyl)-$CONMe_2$
$(CH_3$—$CH_2)_2$C(O-phenyl)-$CONMe_2$
$(CH_3$—$CH_2)_2$C(O-benzyl)-$CONMe_2$
$CH_3$—$CH_2$—$CH_2$—CH(O-Me)-$CONMe_2$
$CH_3$—$CH_2$—$CH_2$—CH(O-Et)-$CONMe_2$
$CH_3$—$CH_2$—$CH_2$—CH(O-n-propyl)-$CONMe_2$
$CH_3$—$CH_2$—$CH_2$—CH(O-isopropyl)-$CONMe_2$
$CH_3$—$CH_2$—$CH_2$—CH(O-n-butyl)-$CONMe_2$
$CH_3$—$CH_2$—$CH_2$—CH(O-isobutyl)-$CONMe_2$
$CH_3$—$CH_2$—$CH_2$—CH(O-tertbutyl)-$CONMe_2$
$CH_3$—$CH_2$—$CH_2$—CH(O-n-pentyl)-$CONMe_2$
$CH_3$—$CH_2$—$CH_2$—CH(O-isopentyl)-$CONMe_2$
$CH_3$—$CH_2$—$CH_2$—CH(O-isoamyl)-$CONMe_2$ CH₃—CH₂—CH₂—CH(O-n-hexyl)-CONMe₂
CH₃—CH₂—CH₂—CH(O-cyclohexyl)-CONMe₂
CH₃—CH₂—CH₂—CH(O-n-octyl)-CONMe₂
CH₃—CH₂—CH₂—CH(O-isooctyl)-CONMe₂
CH₃—CH₂—CH₂—CH(O-2-ethylhexyl)-CONMe₂
CH₃—CH₂—CH₂—CH(O-decyl)-CONMe₂
CH₃—CH₂—CH₂—CH(O-dodecyl)-CONMe₂
CH₃—CH₂—CH₂—CH(O-phenyl)-CONMe₂
CH₃—CH₂—CH₂—CH(O-benzyl)-CONMe₂
CH₃—CH₂—CH₂—CMe(O-Me)-CONMe₂
CH₃—CH₂—CH₂—CMe(O-Et)-CONMe₂
CH₃—CH₂—CH₂—CMe(O-n-propyl)-CONMe₂
CH₃—CH₂—CH₂—CMe(O-isopropyl)-CONMe₂
CH₃—CH₂—CH₂—CMe(O-n-butyl)-CONMe₂
CH₃—CH₂—CH₂—CMe(O-isobutyl)-CONMe₂
CH₃—CH₂—CH₂—CMe(O-tertbutyl)-CONMe₂
CH₃—CH₂—CH₂—CMe(O-n-pentyl)-CONMe₂
CH₃—CH₂—CH₂—CMe(O-isopentyl)-CONMe₂
CH₃—CH₂—CH₂—CMe(O-isoamyl)-CONMe₂
CH₃—CH₂—CH₂—CMe(O-n-hexyl)-CONMe₂
CH₃—CH₂—CH₂—CMe(O-cyclohexyl)-CONMe₂
CH₃—CH₂—CH₂—CMe(O-n-octyl)-CONMe₂
CH₃—CH₂—CH₂—CMe(O-isooctyl)-CONMe₂
CH₃—CH₂—CH₂—CMe(O-2-ethylhexyl)-CONMe₂
CH₃—CH₂—CH₂—CMe(O-decyl)-CONMe₂
CH₃—CH₂—CH₂—CMe(O-dodecyl)-CONMe₂
CH₃—CH₂—CH₂—CMe(O-phenyl)-CONMe₂
CH₃—CH₂—CH₂—CMe(O-benzyl)-CONMe₂
CH₃—CH₂—CH₂—CEt(O-Me)-CONMe₂
CH₃—CH₂—CH₂—CEt(O-Et)-CONMe₂
CH₃—CH₂—CH₂—CEt(O-n-propyl)-CONMe₂
CH₃—CH₂—CH₂—CEt(O-isopropyl)-CONMe₂
CH₃—CH₂—CH₂—CEt(O-n-butyl)-CONMe₂
CH₃—CH₂—CH₂—CEt(O-isobutyl)-CONMe₂
CH₃—CH₂—CH₂—CEt(O-tertbutyl)-CONMe₂
CH₃—CH₂—CH₂—CEt(O-n-pentyl)-CONMe₂
CH₃—CH₂—CH₂—CEt(O-isopentyl)-CONMe₂
CH₃—CH₂—CH₂—CEt(O-isoamyl)-CONMe₂
CH₃—CH₂—CH₂—CEt(O-n-hexyl)-CONMe₂
CH₃—CH₂—CH₂—CEt(O-cyclohexyl)-CONMe₂
CH₃—CH₂—CH₂—CEt(O-n-octyl)-CONMe₂
CH₃—CH₂—CH₂—CEt(O-isooctyl)-CONMe₂
CH₃—CH₂—CH₂—CEt(O-2-ethylhexyl)-CONMe₂
CH₃—CH₂—CH₂—CEt(O-decyl)-CONMe₂
CH₃—CH₂—CH₂—CEt(O-dodecyl)-CONMe₂
CH₃—CH₂—CH₂—CEt(O-phenyl)-CONMe₂
CH₃—CH₂—CH₂—CEt(O-benzyl)-CONMe₂
(CH₃—CH₂—CH₂)₂C(O-Me)-CONMe₂
(CH₃—CH₂—CH₂)₂C(O-Et)-CONMe₂
(CH₃—CH₂—CH₂)₂C(O-n-propyl)-CONMe₂
(CH₃—CH₂—CH₂)₂C(O-isopropyl)-CONMe₂
(CH₃—CH₂—CH₂)₂C(O-n-butyl)-CONMe₂
(CH₃—CH₂—CH₂)₂C(O-isobutyl)-CONMe₂
(CH₃—CH₂—CH₂)₂C(O-tertbutyl)-CONMe₂
(CH₃—CH₂—CH₂)₂C(O-n-pentyl)-CONMe₂
(CH₃—CH₂—CH₂)₂C(O-isopentyl)-CONMe₂
(CH₃—CH₂—CH₂)₂C(O-isoamyl)-CONMe₂
(CH₃—CH₂—CH₂)₂C(O-n-hexyl)-CONMe₂
(CH₃—CH₂—CH₂)₂C(O-cyclohexyl)-CONMe₂
(CH₃—CH₂—CH₂)₂C(O-n-octyl)-CONMe₂
(CH₃—CH₂—CH₂)₂C(O-isooctyl)-CONMe₂
(CH₃—CH₂—CH₂)₂C(O-2-ethylhexyl)-CONMe₂
(CH₃—CH₂—CH₂)₂C(O-decyl)-CONMe₂
(CH₃—CH₂—CH₂)₂C(O-dodecyl)-CONMe₂
(CH₃—CH₂—CH₂)₂C(O-phenyl)-CONMe₂
(CH₃—CH₂—CH₂)₂C(O-benzyl)-CONMe₂
CH₃—CH(O-Et)-CONEt₂
CH₃—CH(O-n-propyl)-CONEt₂
CH₃—CH(O-isopropyl)-CONEt₂
CH₃—CH(O-isobutyl)-CONEt₂
CH₃—CH(O-tertbutyl)-CONEt₂
CH₃—CH(O-n-pentyl)-CONEt₂
CH₃—CH(O-isopentyl)-CONEt₂
CH₃—CH(O-isoamyl)-CONEt₂
CH₃—CH(O-n-hexyl)-CONEt₂
CH₃—CH(O-cyclohexyl)-CONEt₂
CH₃—CH(O-n-octyl)-CONEt₂
CH₃—CH(O-isooctyl)-CONEt₂
CH₃—CH(O-2-ethylhexyl)-CONEt₂
CH₃—CH(O-decyl)-CONEt₂
CH₃—CH(O-dodecyl)-CONEt₂
CH₃—CH(O-phenyl)-CONEt₂
CH₃—CH(O-benzyl)-CONEt₂
CH₂(O-Et)-CONEt₂
CH₂(O-n-propyl)-CONEt₂
CH₂(O-isopropyl)-CONEt₂
CH₂(O-isobutyl)-CONEt₂
CH₂(O-tertbutyl)-CONEt₂
CH₂(O-n-pentyl)-CONEt₂
CH₂(O-isopentyl)-CONEt₂
CH₂(O-isoamyl)-CONEt₂
CH₂(O-n-hexyl)-CONEt₂
CH₂(O-cyclohexyl)-CONEt₂
CH₂(O-n-octyl)-CONEt₂
CH₂(O-isooctyl)-CONEt₂
CH₂(O-2-ethylhexyl)-CONEt₂
CH₂(O-decyl)-CONEt₂
CH₂(O-dodecyl)-CONEt₂
CH₂(O-phenyl)-CONEt₂
CH₂(O-benzyl)-CONEt₂
(CH₃)₂C(O-Me)-CONEt₂
(CH₃)₂C(O-Et)-CONEt₂
(CH₃)₂C(O-n-propyl)-CONEt₂
(CH₃)₂C(O-isopropyl)-CONEt₂
(CH₃)₂C(O-n-butyl)-CONEt₂
(CH₃)₂C(O-isobutyl)-CONEt₂
(CH₃)₂C(O-tertbutyl)-CONEt₂
(CH₃)₂C(O-n-pentyl)-CONEt₂
(CH₃)₂C(O-isopentyl)-CONEt₂
(CH₃)₂C(O-isoamyl)-CONEt₂
(CH₃)₂C(O-n-hexyl)-CONEt₂
(CH₃)₂C(O-cyclohexyl)-CONEt₂
(CH₃)₂C(O-n-octyl)-CONEt₂
(CH₃)₂C(O-isooctyl)-CONEt₂
(CH₃)₂C(O-2-ethylhexyl)-CONEt₂
(CH₃)₂C(O-decyl)-CONEt₂
(CH₃)₂C(O-dodecyl)-CONEt₂
(CH₃)₂C(O-phenyl)-CONEt₂
(CH₃)₂C(O-benzyl)-CONEt₂
CH₃—CH₂—CH(O-Me)-CONEt₂
CH₃—CH₂—CH(O-Et)-CONEt₂
CH₃—CH₂—CH(O-n-propyl)-CONEt₂
CH₃—CH₂—CH(O-isopropyl)-CONEt₂
CH₃—CH₂—CH(O-n-butyl)-CONEt₂
CH₃—CH₂—CH(O-isobutyl)-CONEt₂
CH₃—CH₂—CH(O-tertbutyl)-CONEt₂
CH₃—CH₂—CH(O-n-pentyl)-CONEt₂
CH₃—CH₂—CH(O-isopentyl)-CONEt₂
CH₃—CH₂—CH(O-isoamyl)-CONEt₂
CH₃—CH₂—CH(O-n-hexyl)-CONEt₂
CH₃—CH₂—CH(O-cyclohexyl)-CONEt₂
CH₃—CH₂—CH(O-n-octyl)-CONEt₂
CH₃—CH₂—CH(O-isooctyl)-CONEt₂
CH₃—CH₂—CH(O-2-ethylhexyl)-CONEt₂

CH₃—CH₂—CH(O-decyl)-CONEt₂
CH₃—CH₂—CH(O-dodecyl)-CONEt₂
CH₃—CH₂—CH(O-phenyl)-CONEt₂
CH₃—CH₂—CH(O-benzyl)-CONEt₂
CH₃—CH₂—CMe(O-Me)-CONEt₂
CH₃—CH₂—CMe(O-Et)-CONEt₂
CH₃—CH₂—CMe(O-n-propyl)-CONEt₂
CH₃—CH₂—CMe(O-isopropyl)-CONEt₂
CH₃—CH₂—CMe(O-n-butyl)-CONEt₂
CH₃—CH₂—CMe(O-isobutyl)-CONEt₂
CH₃—CH₂—CMe(O-tertbutyl)-CONEt₂
CH₃—CH₂—CMe(O-n-pentyl)-CONEt₂
CH₃—CH₂—CMe(O-isopentyl)-CONEt₂
CH₃—CH₂—CMe(O-isoamyl)-CONEt₂
CH₃—CH₂—CMe(O-n-hexyl)-CONEt₂
CH₃—CH₂—CMe(O-cyclohexyl)-CONEt₂
CH₃—CH₂—CMe(O-n-octyl)-CONEt₂
CH₃—CH₂—CMe(O-isooctyl)-CONEt₂
CH₃—CH₂—CMe(O-2-ethylhexyl)-CONEt₂
CH₃—CH₂—CMe(O-decyl)-CONEt₂
CH₃—CH₂—CMe(O-dodecyl)-CONEt₂
CH₃—CH₂—CMe(O-phenyl)-CONEt₂
CH₃—CH₂—CMe(O-benzyl)-CONEt₂
(CH₃—CH₂)₂C(O-Me)-CONEt₂
(CH₃—CH₂)₂C(O-Et)-CONEt₂
(CH₃—CH₂)₂C(O-n-propyl)-CONEt₂
(CH₃—CH₂)₂C(O-isopropyl)-CONEt₂
(CH₃—CH₂)₂C(O-n-butyl)-CONEt₂
(CH₃—CH₂)₂C(O-isobutyl)-CONEt₂
(CH₃—CH₂)₂C(O-tertbutyl)-CONEt₂
(CH₃—CH₂)₂C(O-n-pentyl)-CONEt₂
(CH₃—CH₂)₂C(O-isopentyl)-CONEt₂
(CH₃—CH₂)₂C(O-isoamyl)-CONEt₂
(CH₃—CH₂)₂C(O-n-hexyl)-CONEt₂
(CH₃—CH₂)₂C(O-cyclohexyl)-CONEt₂
(CH₃—CH₂)₂C(O-n-octyl)-CONEt₂
(CH₃—CH₂)₂C(O-isooctyl)-CONEt₂
(CH₃—CH₂)₂C(O-2-ethylhexyl)-CONEt₂
(CH₃—CH₂)₂C(O-decyl)-CONEt₂
(CH₃—CH₂)₂C(O-dodecyl)-CONEt₂
(CH₃—CH₂)₂C(O-phenyl)-CONEt₂
(CH₃—CH₂)₂C(O-benzyl)-CONEt₂
CH₃—CH₂—CH₂—CH(O-Me)-CONEt₂
CH₃—CH₂—CH₂—CH(O-Et)-CONEt₂
CH₃—CH₂—CH₂—CH(O-n-propyl)-CONEt₂
CH₃—CH₂—CH₂—CH(O-isopropyl)-CONEt₂
CH₃—CH₂—CH₂—CH(O-n-butyl)-CONEt₂
CH₃—CH₂—CH₂—CH(O-isobutyl)-CONEt₂
CH₃—CH₂—CH₂—CH(O-tertbutyl)-CONEt₂
CH₃—CH₂—CH₂—CH(O-n-pentyl)-CONEt₂
CH₃—CH₂—CH₂—CH(O-isopentyl)-CONEt₂
CH₃—CH₂—CH₂—CH(O-isoamyl)-CONEt₂
CH₃—CH₂—CH₂—CH(O-n-hexyl)-CONEt₂
CH₃—CH₂—CH₂—CH(O-cyclohexyl)-CONEt₂
CH₃—CH₂—CH₂—CH(O-n-octyl)-CONEt₂
CH₃—CH₂—CH₂—CH(O-isooctyl)-CONEt₂
CH₃—CH₂—CH₂—CH(O-2-ethylhexyl)-CONEt₂
CH₃—CH₂—CH₂—CH(O-decyl)-CONEt₂
CH₃—CH₂—CH₂—CH(O-dodecyl)-CONEt₂
CH₃—CH₂—CH₂—CH(O-phenyl)-CONEt₂
CH₃—CH₂—CH₂—CH(O-benzyl)-CONEt₂
CH₃—CH₂—CH₂—CMe(O-Me)-CONEt₂
CH₃—CH₂—CH₂—CMe(O-Et)-CONEt₂
CH₃—CH₂—CH₂—CMe(O-n-propyl)-CONEt₂
CH₃—CH₂—CH₂—CMe(O-isopropyl)-CONEt₂
CH₃—CH₂—CH₂—CMe(O-n-butyl)-CONEt₂
CH₃—CH₂—CH₂—CMe(O-isobutyl)-CONEt₂
CH₃—CH₂—CH₂—CMe(O-tertbutyl)-CONEt₂
CH₃—CH₂—CH₂—CMe(O-n-pentyl)-CONEt₂
CH₃—CH₂—CH₂—CMe(O-isopentyl)-CONEt₂
CH₃—CH₂—CH₂—CMe(O-isoamyl)-CONEt₂
CH₃—CH₂—CH₂—CMe(O-n-hexyl)-CONEt₂
CH₃—CH₂—CH₂—CMe(O-cyclohexyl)-CONEt₂
CH₃—CH₂—CH₂—CMe(O-n-octyl)-CONEt₂
CH₃—CH₂—CH₂—CMe(O-isooctyl)-CONEt₂
CH₃—CH₂—CH₂—CMe(O-2-ethylhexyl)-CONEt₂
CH₃—CH₂—CH₂—CMe(O-decyl)-CONEt₂
CH₃—CH₂—CH₂—CMe(O-dodecyl)-CONEt₂
CH₃—CH₂—CH₂—CMe(O-phenyl)-CONEt₂
CH₃—CH₂—CH₂—CMe(O-benzyl)-CONEt₂
CH₃—CH₂—CH₂—CEt(O-Me)-CONEt₂
CH₃—CH₂—CH₂—CEt(O-Et)-CONEt₂
CH₃—CH₂—CH₂—CEt(O-n-propyl)-CONEt₂
CH₃—CH₂—CH₂—CEt(O-isopropyl)-CONEt₂
CH₃—CH₂—CH₂—CEt(O-n-butyl)-CONEt₂
CH₃—CH₂—CH₂—CEt(O-isobutyl)-CONEt₂
CH₃—CH₂—CH₂—CEt(O-tertbutyl)-CONEt₂
CH₃—CH₂—CH₂—CEt(O-n-pentyl)-CONEt₂
CH₃—CH₂—CH₂—CEt(O-isopentyl)-CONEt₂
CH₃—CH₂—CH₂—CEt(O-isoamyl)-CONEt₂
CH₃—CH₂—CH₂—CEt(O-n-hexyl)-CONEt₂
CH₃—CH₂—CH₂—CEt(O-cyclohexyl)-CONEt₂
CH₃—CH₂—CH₂—CEt(O-n-octyl)-CONEt₂
CH₃—CH₂—CH₂—CEt(O-isooctyl)-CONEt₂
CH₃—CH₂—CH₂—CEt(O-2-ethylhexyl)-CONEt₂
CH₃—CH₂—CH₂—CEt(O-decyl)-CONEt₂
CH₃—CH₂—CH₂—CEt(O-dodecyl)-CONEt₂
CH₃—CH₂—CH₂—CEt(O-phenyl)-CONEt₂
CH₃—CH₂—CH₂—CEt(O-benzyl)-CONEt₂
(CH₃—CH₂—CH₂)₂C(O-Me)-CONEt₂
(CH₃—CH₂—CH₂)₂C(O-Et)-CONEt₂
(CH₃—CH₂—CH₂)₂C(O-n-propyl)-CONEt₂
(CH₃—CH₂—CH₂)₂C(O-isopropyl)-CONEt₂
(CH₃—CH₂—CH₂)₂C(O-n-butyl)-CONEt₂
(CH₃—CH₂—CH₂)₂C(O-isobutyl)-CONEt₂
(CH₃—CH₂—CH₂)₂C(O-tertbutyl)-CONEt₂
(CH₃—CH₂—CH₂)₂C(O-n-pentyl)-CONEt₂
(CH₃—CH₂—CH₂)₂C(O-isopentyl)-CONEt₂
(CH₃—CH₂—CH₂)₂C(O-isoamyl)-CONEt₂
(CH₃—CH₂—CH₂)₂C(O-n-hexyl)-CONEt₂
(CH₃—CH₂—CH₂)₂C(O-cyclohexyl)-CONEt₂
(CH₃—CH₂—CH₂)₂C(O-n-octyl)-CONEt₂
(CH₃—CH₂—CH₂)₂C(O-isooctyl)-CONEt₂
(CH₃—CH₂—CH₂)₂C(O-2-ethylhexyl)-CONEt₂
(CH₃—CH₂—CH₂)₂C(O-decyl)-CONEt₂
(CH₃—CH₂—CH₂)₂C(O-dodecyl)-CONEt₂
(CH₃—CH₂—CH₂)₂C(O-phenyl)-CONEt₂
(CH₃—CH₂—CH₂)₂C(O-benzyl)-CONEt₂

The novel compounds of the invention may notably be selected from the following compounds:

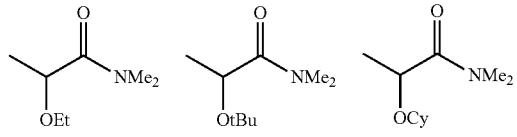

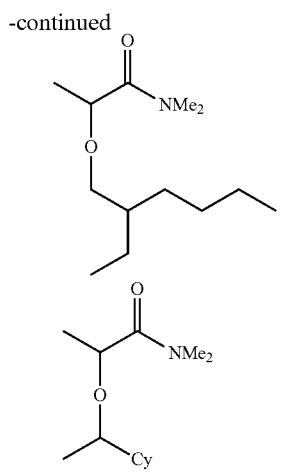

Method for Preparing the Compound

The compound of formula (I) may be prepared by any suitable method. The method may further comprise one of the following steps or both of them:

step a) an amidation step with which the group —CONR$^1$R$^2$ may be obtained, and/or step b) a nucleophilic substitution or addition step with which the group —OR$^1$ may be obtained.

Steps a) and b) may be applied in the order a) and then b) or in the order b) and then a). However performing a) and then b) is preferred.

The steps may be applied from a starting product comprising:
- a group R$^a$R$^b$CZ$^1$—, wherein Z$^1$ is a nucleophilic and/or nucleofugic group
- a group —CO—Z$^2$ wherein Z$^2$ is a group selected from OR', Cl, wherein R' is a hydrogen or an alkyl group, preferably a C$_1$-C$_4$ alkyl group, for example a methyl or ethyl group.

Particularly useful starting products are the products of the following formula (I'):

$$R^aR^bCZ^1\text{—CO—}Z^2 \qquad (I')$$

As an example, mention may be made of glycolic acid, methyl glycolate, ethyl glycolate, lactic acid, methyl lactate, ethyl lactate, methyl chloropropanoate. Such products are available commercially. It is mentioned that glycolic acid or its ester may be obtained from sugar cane, and that lactic acid or its ester may be obtained from milk. These products may alternatively be obtained via a microbiological route. These are particularly suitable renewable materials.

Step a) Amidation

Step a) is an amidation step. Typically it allows transformation of a group —CO—Z$^2$ into a group —CONR$^2$R$^3$. It is typically applied by means of an amine of formula HNR$^2$R$^3$.

This step may notably be applied by transforming the group —COOH into a group —CONR$^2$R$^3$ directly by reaction with an amine of formula HNR$^2$R$^3$ or by forming a group —COCl and then by reacting with an amine of formula HNR$^2$R$^3$, so as to obtain the compound of formula (I).

It is notably possible to apply the following sequence: the —COOH group is transformed into a —CONR$^2$R$^3$ group directly by reaction with an amine of formula HNR$^2$R$^3$.

It is also possible to perform trans-amidation. This may be applied in a known way. During this reaction, typically 0.8 to 1.2 mole, preferably from 0.9 to 1.1 mole, preferably about 1 mole of amine per mole of ester are preferably applied. Notably, it is possible to apply acid catalysts (notably Lewis acids) or basic catalysts, for example potassium carbonate or alkyl ortho-titanates. This step may be applied in a solution, for example in an aqueous solution, or in a solution in toluene. During this step it is possible to gradually remove the methanol formed in order to promote the reaction. The removal may be accompanied by removal of the solvent, for example by forming an azeotrope. After separation of the methanol, the removed solvent may be reintroduced into the process.

Step b) Nucleophilic Substitution or Addition

Step b) is a nucleophilic substitution or addition step. Typically, it allows a group R$^a$R$^b$CZ$^1$-group to be transformed into an —OR$^1$. Nucleophilic substitutions and additions are reactions known to one skilled in the art. They may be applied in the presence of an acid or a base, in a known way. A few details are given below.

b$^1$) Nucleophilic Substitution

Within the scope of nucleophilic substitution, according to a first embodiment, the nucleophilic group is a group Z$^1$=OH, put into the presence of a compound R$^1$—Y comprising a nucleofugic group Y (leaving group). As examples of compounds comprising a nucleofugic group, for example mention may be made of compounds of formula R$^1$O—X—OR$^1$ wherein X is —CO— or —SO$_2$—, the compounds of formula R$^1$—X wherein X is a halogen such as Br, Cl, I, the compounds R$^1$—OH.

For example, it is possible to apply the following reaction schemes (wherein Z'$^2$=Z$^2$ or —NR$^1$R$^2$):

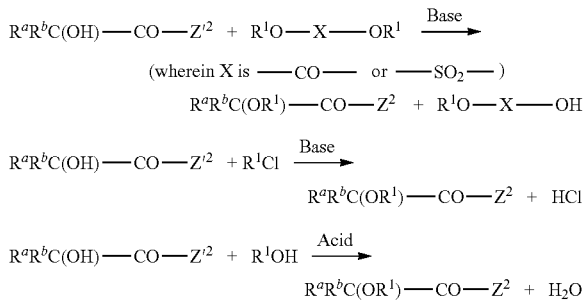

Within the scope of nucleophilic substitution, according to a second embodiment, the nucleophilic compound is an alcohol HOR$^1$ put into the presence of a precursor compound of the compound of formula (I) and bearing a nucleofugic group Z$^1$ instead of the future —OR$^1$ group. As a nucleofugic group Z$^1$, mention may for example be made of halogen atoms such as Br, Cl, I and of X—OR groups wherein X=CO or SO$_2$ and R is an alkyl or an aromatic group, for example a mesylate or tosylate or carbonate group. This embodiment may for example be applied starting from a compound of formula R$^a$R$^b$CCl—CO—Me, obtained by radical chlorination of a compound of formula R$^a$R$^b$CH—CO—OMe. This embodiment may also be applied starting from a compound of formula R$^a$R$^b$CCl—CONR$^1$R$^2$, obtained by radical chlorination of a compound of formula R$^a$R$^b$CH—CONR$^1$R$^2$.

b$^2$) Nucleophilic Addition

Within the scope of a nucleophilic addition, the nucleophilic group is a group Z$^1$=OH, put into the presence of a compound having one ethylenic unsaturation (R$^1$ corresponding to said saturated compound).

For example it is possible to apply the following reaction scheme (wherein $Z'^2=Z^2$ or $—NR^1R^2$):

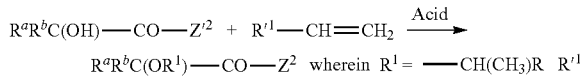

Uses—Formulations

The compound of the invention may notably be used as a surfactant, solvent, co-solvent and/or crystallization inhibitor, as a plasticizer or as a coalescence agent.

By co-solvent is meant that other solvents may be associated with it. The use as a solvent or co-solvent notably comprises uses for dissolving a compound in a formulation, in a reaction medium, the use for totally or partly solubilizing a product to be removed (degreasing, stripping), and/or for facilitating detachment of material films.

For the use as a surfactant, alkoxylated and/or propoxylated compounds are preferred, i.e. wherein n is different from 0 in formula (I).

The compound of the invention may notably be used, for the functions indicated above or for other functions, in a phytosanitary formulation, in a cleaning formulation, in a stripping formulation, in a degreasing formulation, in a formulation of lubricants for textiles, in a coating formulation, for example in a paint formulation, in a formulation of pigments or ink, in a plastic formulation.

The compound may for example be use as a coalescence agent in an aqueous paint formulation.

The compound may notably be used as a solvent for resins for example in the cable cladding industry or in the electronics industry, notably as a solvent of PVDF.

The compound may notably be used as a cleaning and/or stripping solvent in the electronics industry. It may notably be used in lithium batteries. It may notably be used on photoresist resins, polymers, waxes, fats, or oils.

The compound may notably be used for cleaning inks, for example upon producing inks or during the use of ink for printing.

The compound may notably be used for cleaning sieves or other tools applied in methods for making and/or recycling paper.

The compound may notably be used for cleaning bitumens or bituminous sands ("tar sands") for example on coated substrates, on the tools used for applying these materials, on soiled clothing, on dirty vehicles.

The compound may notably be used for cleaning flying machines such as aircraft, helicopters, space shuttles.

The compound may notably be used as a degreasing agent on metal surfaces, for example surfaces of tools, of manufactured objects, of metal sheets, of molds, notably in steel or in aluminium or in alloys of these metals.

The compound may notably be used as a cleaning solvent on hard surfaces or on textile surfaces.

The compound may notably be used as a solvent for stripping paint or resins, on tool surfaces, for example casting molds, on surfaces of industrial sites, (floors, partitions, etc.). The formulations for stripping paints may notably be formulations with an aqueous base (the compound being mixed with water) or with a solvent base (the compound then being the solvent or a compound mixed with water).

The compound may notably be used as a plasticizer in formulations of thermoplastic polymers.

The cleaning and/or degreasing formulations may notably be formulations for housekeeping performed in households or in public domains (hotels, offices, factories . . . ). This may be a formulation for cleaning hard surfaces such as floors, furniture surfaces and those fitting out kitchens and bathrooms, dishes. These formulations may also be used in the industrial sphere for degreasing manufactured products and/or cleaning them. Such formulations may notably be used for cleaning and/or cleansing products, tools, molds, clothing or other articles.

The compound of the invention may notably be used in phytosanitary formulations comprising a solid active product. More details are given below, where the term of "solvent" may designate the compound of the invention or a material composition comprising it, described above.

Detailed use within the Scope of Phytosanitary Formulations

The phytosanitary formulation is generally a concentrated phytosanitary formulation comprising an active compound.

Agriculture uses many active materials such as fertilizers or pesticides, for example insecticides, herbicides or fungicides. They are referred to as active phytosanitary products (or active materials). Active phytosanitary products are generally produced in pure or highly concentrated form. They have to be used on farms with low concentrations, for this purpose they are generally formulated with other ingredients in order to allow easy weight dilution by the farmer. These are referred to as phytosanitary formulations. The dilution performed by the farmer is generally achieved by mixing the phytosanitary formulation with water.

Thus, phytosanitary formulations should allow easy weight dilution by the farmer, in order to obtain a product in which the phytosanitary product is correctly dispersed, for example as a solution, an emulsion, suspension or suspoemulsion. With phytosanitary formulations, it is thereby possible to transport a phytosanitary product in a relatively concentrated form, with easy conditioning and/or easy handling by the final user. Different types of phytosanitary formulations may be used according to the different phytosanitary products. For example mention may be made of emulsifiable concentrates (EC), concentrated emulsions (Emulsion in Water "EW"), micro-emulsions (ME), wettable powders (WP), water-dispersible granules (WDG). The formulations which may be used depend on the physical form of the phytosanitary product (for example a solid or a liquid) and on its physico-chemical properties in the presence of other compounds such as water or solvents.

After weight dilution by the farmer, for example by mixing with water, the phytosanitary product may exist in different physical forms; solution, dispersion of solid particles, dispersion of droplets of the product, droplets of solvent in which the product is dissolved. The phytosanitary formulations generally comprise compounds with which these physical forms may be obtained. These may for example be surfactants, solvents, mineral supports and/or dispersants. Very often, these compounds do not have an active nature, but an intermediate nature for assisting with the formulation. The phytosanitary formulations may notably be in liquid form or in solid form.

In order to prepare phytosanitary formulations of solid active phytosanitary products, it is known how to solubilize the product in a solvent. The phytosanitary formulation thus comprises a solution of the product in the solvent. The formulation may be in solid form, for example as a wettable powder (WP) where the solution impregnates an inorganic support, for example kaolin and/or silica. The formulation may alternatively be in liquid form, for example in the form of an emulsifiable concentrate (EC) having a single limpid liquid phase comprising the solvent and the product in the solution, which may form an emulsion by adding water, without stirring or with low stirring. It may also be in the form of a cloudy concentrated emulsion (EW), the phase of which dispersed in the water comprises the solvent and the product in solution in the solvent. It may also be in the form of a limpid micro-emulsion (ME), the phase of which dispersed in water comprises the solvent and the product in solution in the solvent.

Certain solid phytosanitary actives are often difficult to formulate. For example, tebuconazole is a particularly efficient fungicide and of widespread use, notably for cultivation of soya. For certain phytosanitary actives, it is difficult to make concentrated formulations, easy to dilute for the farmer, stable and without substantial (proven or perceived) drawbacks as regards safety, toxicity and/or ecotoxicity. For certain actives, it is difficult to formulate them at relatively high concentrations, with sufficient stability. In particular, it is necessary to avoid the occurrence of crystals in particular at low temperature and/or during dilution and/or during storage at a high temperature of the diluted composition. The crystals may have negative effects, notably clogging the filters of the devices used for distributing the diluted composition, clogging the spray devices, reducing the overall activity of the formulation, generating unnecessary problems of waste management for removing the crystals, and/or causing poor distribution of the active product on the farm field.

The formulations comprising the solvent notably have:

solubilization of significant amounts of actives, absence of crystallization, even in demanding conditions, good biological activity which may be due to good solvation, and/or a safety, toxicology, and/or ecotoxicology profile perceived as favorable.

The phytosanitary formulation may further be a concentrated phytosanitary formulation comprising:

a) an active phytosanitary product, b) the solvent c) optionally at least one emulsifier, preferably a surfactant, and d) optionally water.

The phytosanitary formulation of the invention may notably be in the form of an emulsifiable concentrate (EC), a concentrated micro-emulsion preferably in water (ME) or a concentrated emulsion preferably in water (EW).

Active Phytosanitary Product a)

Active phytosanitary products, notably products not soluble in water, and solid products are known to one skilled in the art. The active phytosanitary product may notably be a herbicide, an insecticide, an acaricide, a fungicide, or a rodenticide for example a raticide.

As non-limiting examples of suitable active materials, mention may be made inter alia of Ametryne, Diuron, Linuron, Chlortoluron, Isoproturon, Nicosulfuron, Metamitron, Diazinon, Aclonifen, Atrazine, Chlorothalonil, Bromoxynil, Bromoxynil heptanoate, Bromoxynil octanoate, Mancozeb, Maneb, Zineb, Phenmedipham, Propanyl, the series of phenoxyphenoxy agents, the series of heteroaryloxyphenoxy agents, CMPP, MCPA, 2,4-D, Simazine, active products from the series of imidazolinones, family of organophosphorus agents, with notably Azinphos-ethyl, Azinphos-methyl, Alachlor, Chlorpyriphos, Diclofop-methyl, Fenoxaprop-p-ethyl, Methoxychlore, Cypermethrin, Fenoxycarb, cymoxanil, chlorothalonil, neonicotinoid insecticides, the family of triazole fungicides such as azaconazole, bromuconazole, cyproconazole, difenoconazole, diniconazole, epoxyconazole, fenbuconazole, flusilazole, myclobutanyl, tebuconazole, triadimefon, triadimenol, strobilurins such as pyraclostrobin, picoxystrobin, azoxystrobin, famoxadone, kresoxym-methyl and trifloxystrobin, sulfonylureas such as bensulfuron-methyl, chlorimuron-ethyl, chlorsulfuron, metsulfuron-methyl, nicosulfuron, sulfomethuron-methyl, triasulfuron, tribenuron-methyl.

Preferably non-water-soluble products are preferably selected from this list.

The following active phytosanitary products may notably be applied:

Alachlor

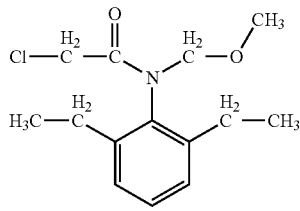 [SMILES: CCc1cccc(CC)c1N(COC)C(=O)CCl]

Chlorpyrifos

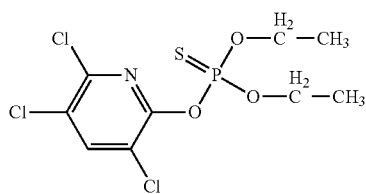 [SMILES: CCOP(=S)(OCC)Oc1nc(Cl)c(Cl)cc1Cl]

-continued
alpha-Cypermethrine
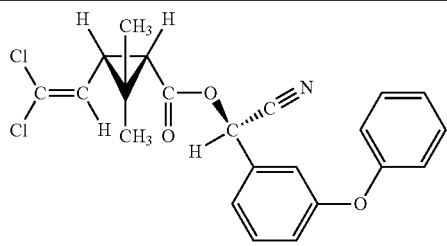
(R)-alcohol (1S)-cis-acid
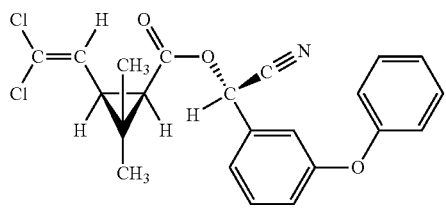
(S)-alcohol (1R)-cis-acid
As a racemic mixture and/or as isolated stereoisomers.
Phenmedipham
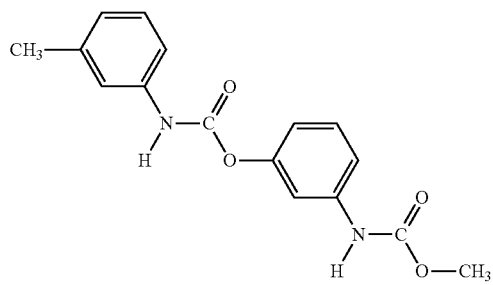
Propanil
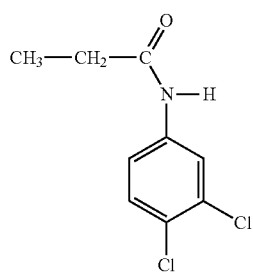
Pendimethalin
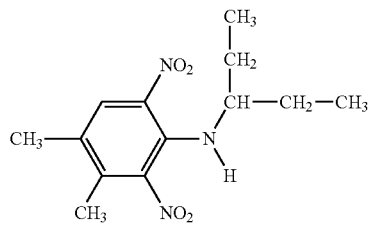
Triadimenol
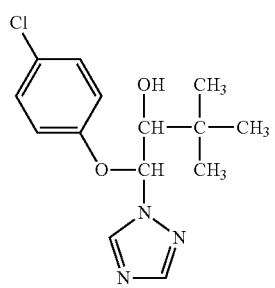 [SMILES: CC(C)(C)C(O)C(Oc1ccc(Cl)cc1)n1cncn1]

-continued
Trifluralin 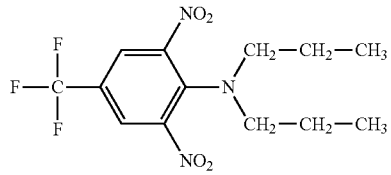 [SMILES: CCCN(CCC)c1c([N+](=O)[O-])cc(C(F)(F)F)cc1[N+](=O)[O-]]
Oxyfluorfen 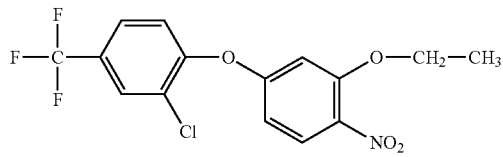 [SMILES: CCOc1cc(Oc2ccc(C(F)(F)F)cc2Cl)ccc1[N+](=O)[O-]]
Dimethoate 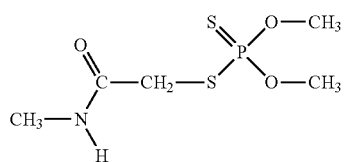
Imidacloprid 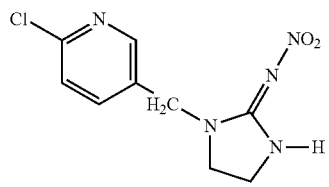 [SMILES: O=[N+]([O-])N=C1NCCN1Cc1ccc(Cl)nc1]
Proxopur 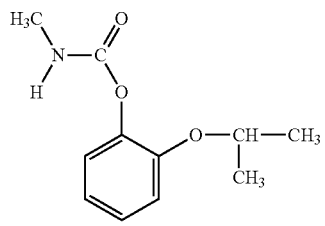
Benomyl 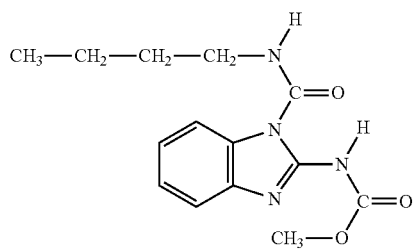 [SMILES: CCCCNC(=O)n1c(NC(=O)OC)nc2ccccc21]
Deltamethrine 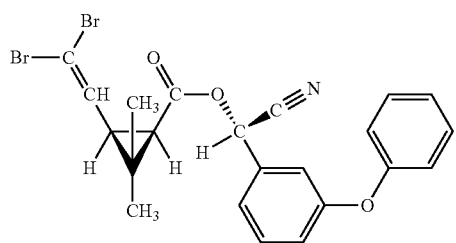
(S)-alcohol (1R)-cis-acid -continued
Fenvalerate 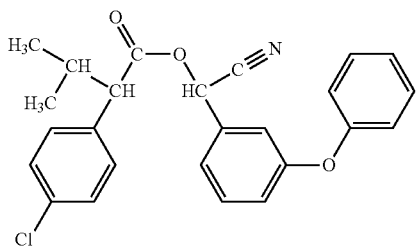 [SMILES: CC(C)C(C(=O)OC(C#N)c1cccc(Oc2ccccc2)c1)c1ccc(Cl)cc1]
Abamectin 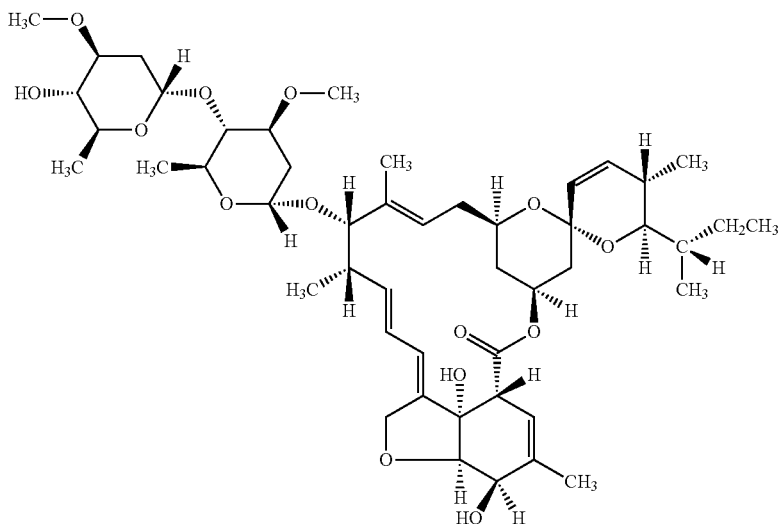
avermectin B<sub>1a</sub>
(major component)
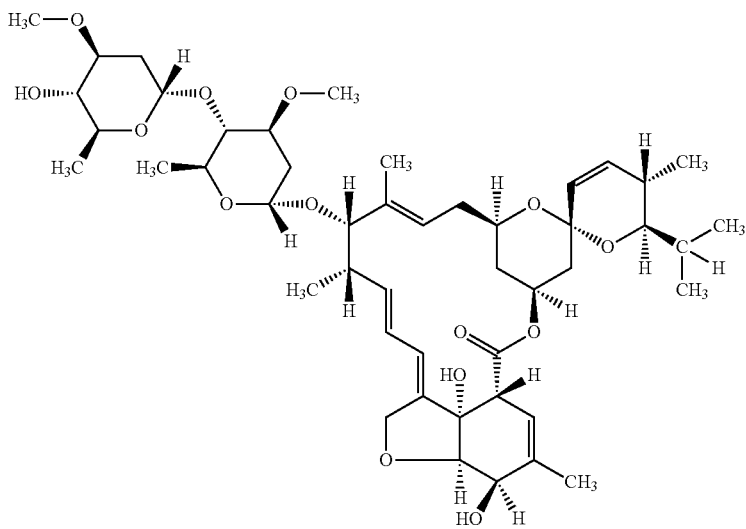
avermectin B<sub>1b</sub>
(minor component)

-continued
Amicarbazone
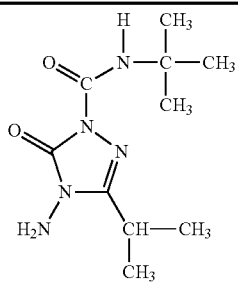
Bifenthrin
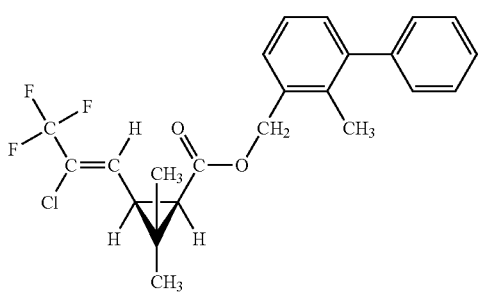
(Z)-(1R)-cis-acid
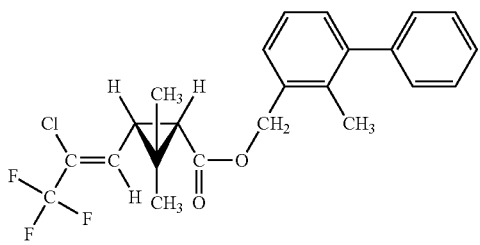
(Z)-(1S)-cis-acid
Carbosulfan
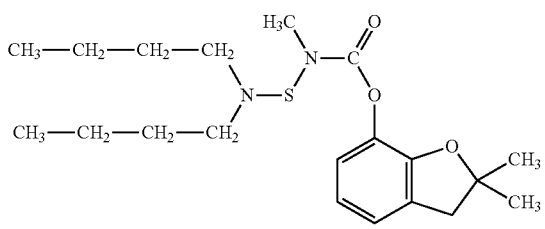 [SMILES: CCCCN(CCCC)SN(C)C(=O)Oc1cccc2c1OC(C)(C)C2]
Cyfluthrin
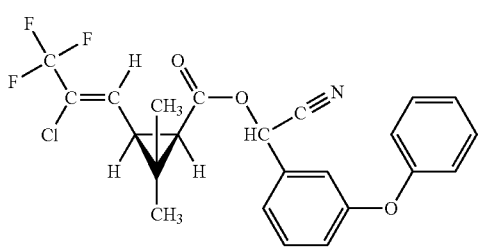
(Z)-(1R)-cis-acid

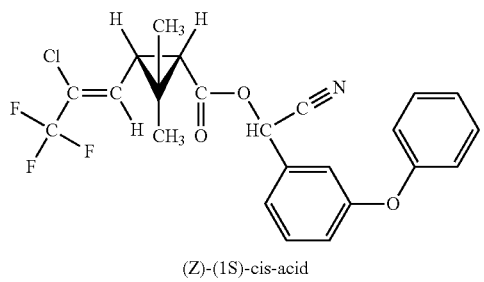 [SMILES: CC1(C)[C@H](/C=C(\Cl)C(F)(F)F)[C@@H]1C(=O)OC(C#N)c1cccc(Oc2ccccc2)c1]
(Z)-(1S)-cis-acid
Difenconazole
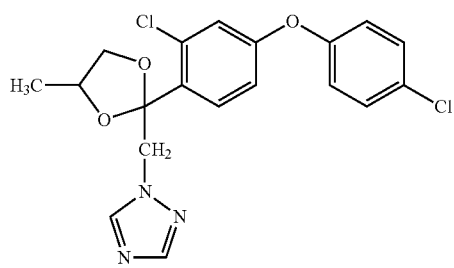 [SMILES: CC1COC(Cn2cncn2)(c2ccc(Oc3ccc(Cl)cc3)cc2Cl)O1]
Ethofenprox
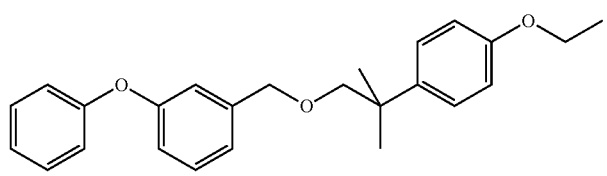 [SMILES: CCOc1ccc(C(C)(C)COCc2cccc(Oc3ccccc3)c2)cc1]
Fenoxaprop-ethyl
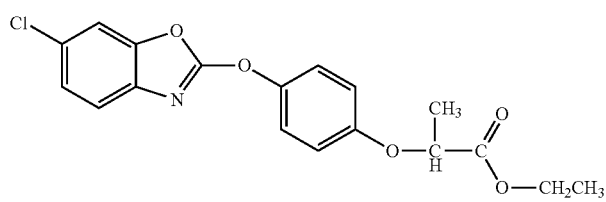 [SMILES: CCOC(=O)C(C)Oc1ccc(Oc2nc3ccc(Cl)cc3o2)cc1]
Fipronil
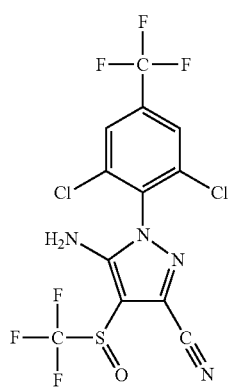 [SMILES: N#Cc1nn(-c2c(Cl)cc(C(F)(F)F)cc2Cl)c(N)c1S(=O)C(F)(F)F]
Fenvalerate
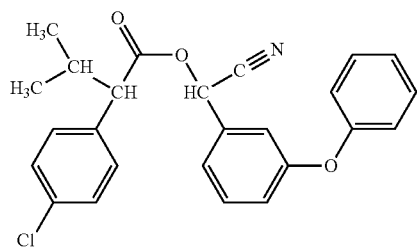 [SMILES: CC(C)C(C(=O)OC(C#N)c1cccc(Oc2ccccc2)c1)c1ccc(Cl)cc1]

-continued
Fluazifop-p-butyl
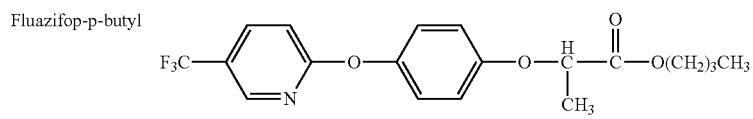
Flufenouron
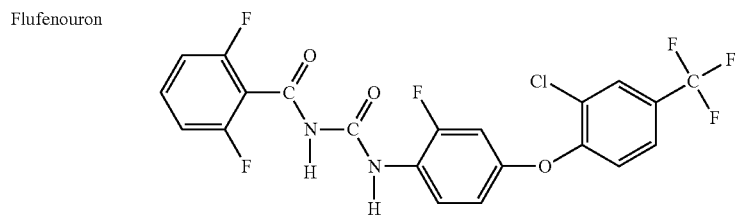
Hexazinone
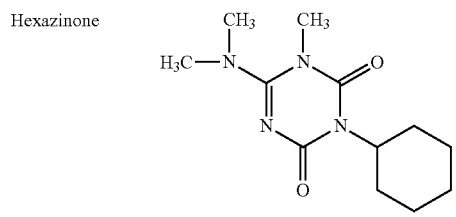
Lambda-cyalothrin
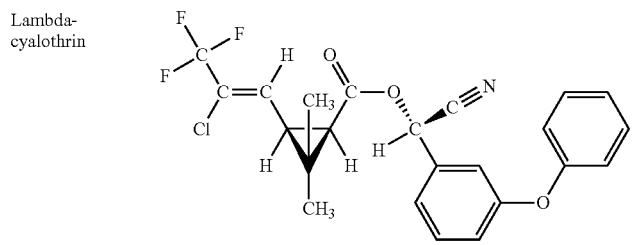
(S)-alcohol (Z)-(1R)-cis-acic
(R)-alcohol (Z)-(1S)-cis-acic
Methomy
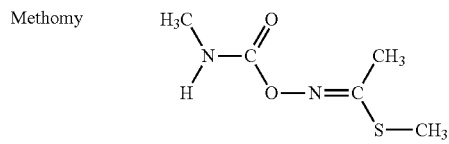
Permethrin
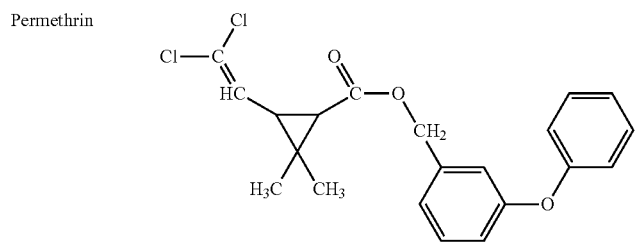

-continued

Prochloraz

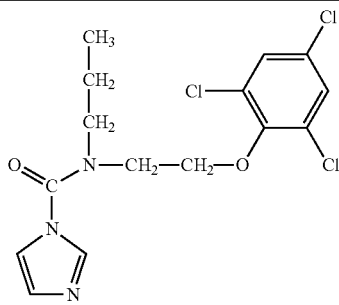

Propiconazole

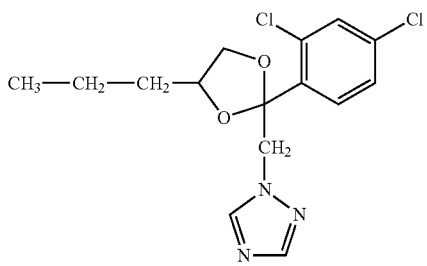 [SMILES: CCCC1COC(Cn2cncn2)(c2ccc(Cl)cc2Cl)O1]

Tebucconazole

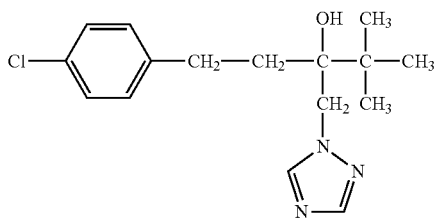

These products and names are known to one skilled in the art. It is possible to combine several active phytosanitary products.

Emulsifying Agent c)

The phytosanitary formulation may comprise an emulsifier, typically and preferably a surfactant. Emulsifiers are agents intended to facilitate emulsification or dispersion after putting the formulation in the presence of water, and/or stabilize (over time and/or in temperature) the emulsion or the dispersion, for example by avoiding sedimentation.

Surfactants are known compounds which have a generally relatively low molar mass, for example of less than 1,000 g/mol. The surfactant may be an anionic surfactant in a salified or acid form, a non-ionic preferably polyalkoxylated, cationic, amphoteric (a term also including zwitterionic surfactants) surfactant. This may be a mixture or a combination of these surfactants.

As examples of anionic surfactants, mention may be made, without intending to be limited thereto, of:
  alkylsulfonic acids, arylsulfonic acids, optionally substituted with one or more hydrocarbon groups, and for which the acid function is partly or totally salified, such as $C_8$-$C_{50}$, more particularly $C_8$-$C_{30}$, preferably $C_{10}$-$C_{22}$ alkylsulfonic acids, benzenesulfonic acids, naphthalenesulfonic acids, substituted with one to three $C_1$-$C_{30}$, preferably $C_4$-$C_{16}$, alkyl groups and/or $C_2C_{30}$, preferably $C_4$-$C_{16}$ alkenyl groups.
  mono- or di-esters of alkylsulfosuccinic acids, for which the linear or branched alkyl portion, optionally substituted with one or more hydroxyl groups and/or linear or branched $C_2$-$C_4$ alkoxylated (preferably ethoxylated, propoxylated, ethopropoxylated) groups.

phosphate esters more particularly selected from those comprising at least one saturated, unsaturated or aromatic, linear or branched hydrocarbon group, comprising from 8 to 40 carbon atoms, preferably 10 to 30, optionally substituted with at least one alkoxylated (ethoxylated, propoxylated, ethopropoxylated) group. Further they comprise at least one mono- or di-esterified phosphate ester so that it is possible to have one or two free or partly or totally salified acid groups. The preferred phosphate esters are of the type of mono- and di-esters of phosphoric acid and of alkoxylated (ethoxylated and/or propoxylated) mono-,di- or tri-styrylphenolaryl phenol, or of alkoxylated (ethoxylated and/or propoxylated) mono-, di- or tri-alkylphenol, optionally substituted with one to four alkyl groups; of phosphoric acid and of a $C_8$-$C_{30}$ alcohol, preferably an alkoxylated (ethoxylated or propoxylated) $C_{10}$-$C_{22}$ alcohol; of phosphoric acid and of a non-alkoxylated $C_8$-$C_{22}$, preferably $C_{10}$-$C_{22}$ alcohol.
sulfate esters obtained from saturated or aromatic alcohols optionally substituted with one or more alkoxylated, (ethoxylated, propxylated, ethopropxylated) groups , and for which the sulfate functions appear in free acid form or partly or totally neutralized. As an example, mention may be made of sulfate esters more particularly obtained from saturated or unsaturated $C_8$-$C_{20}$ alcohols which may comprise 1 to 8 alkoxylated (ethoxylated, propoxylated, ethopropoxylated) units; the sulfate esters obtained from polyalkoxylated phenol, substituted with 1 to 3 saturated or unsaturated $C_2$-$C_{30}$ hydroxy groups, and in which the number of alkoxylated units is comprised between 2 and 40; the sulfate esters obtained from polyalkoxylated mono-, di- or tri-styrylphenol in which the number of alkoxylated units varies from 2 to 40.

The anionic surfactants may be in an acid form (they are potentially anionic) or in a partly or totally salified form, with a counter-ion. The counter-ion may be an alkaline metal, such as sodium or potassium, an earth alkaline metal, such as calcium, or further an ammonium ion of formula $N(R)_4+$ wherein the R radicals, identical or different, represent a hydrogen or a $C_1$-$C_4$ alkyl radical optionally substituted with an oxygen atom.

As examples of non-ionic surfactants, mention may be made without intending to be limited thereto, of:

polyalkoxylated (ethoxylated, propoxylated, ethopropoxylated) phenols substituted with at least one $C_4$-$C_{20}$, preferably $C_4$-$C_1$ alkyl group or substituted with at least one alkylaryl radical for which the alkyl portion is a $C_1$-$C_6$ alkyl. More particularly, the total number of alkoxylated units is comprised between 2 and 100. As an example, mention may be made of polyalkoxylated mono-, di- or tri-(phenylethyl)phenols or polyalkoxylated nonylphenols. Among the ethoxylated and/or propoxylated di- or tri-styrylphenol sulfates and/or phosphates, mention may be made of ethoxylated di-(phenyl-1-ethyl)phenol, containing 10 oxyethylene units, ethoxylated di-(phenyl-1-ethyl)phenol containing 7 oxyethylene units, ethoxylated di-(phenyl-1-ethyl)phenol sulfate, containing 7 oxyethylene units, ethoxylated tri-(phenyl-1-ethyl)phenol, containing 8 oxyethylene units, ethoxylated tri-(phenyl-1-ethyl)phenol, containing 16 oxyethylene units, ethoxylated tri-(phenyl-1-ethyl) phenol sulfate, containing 16 oxyethylene units, ethoxylated tri-(phenyl-1-ethyl)phenol, containing 20 oxyethylene units, ethoxylated tri-(phenyl-1-ethyl)phenol phosphate, containing 16 oxyethylene units.

polyalkoxylated (ethoxylated, propoxylated, ethopropoxylated) $C_6$-$C_{22}$ fatty acids or alcohols. The number of alkoxylated units is comprised between 1 and 60. The ethoxylated fatty acid term includes both the products obtained by ethoxylation of a fatty acid by ethylene oxide and those obtained by esterification of a fatty acid with a polyethylene glycol.

polyalkoxylated (ethoxylated, propoxylated, ethopropoxylated) triglycerides of vegetable or animal origin. Thus triglycerides derived from lard, tallow, ground nut oil, butter oil, cotton seed oil, flax oil, olive oil, palm oil, grape pip oil, fish oil, soya bean oil, castor oil, rape seed oil, copra oil, coconut oil, are suitable and comprise a total number of alkoxylated units comprised between 1 and 60. The term of ethoxylated triglyceride refers to both products obtained by ethoxylation of a triglyceride by ethylene oxide and those obtained by transesterification by a triglyceride with a polyethylene glycol.

sorbitan esters optionally polyalkoxylated (ethoxylated, propoxylated, ethopropoxylated), more particularly esters of cyclized sorbitol and of $C_{10}$—$C_{20}$ fatty acids such as lauric acid, stearic acid or oleic acid, and comprising a total number of alkoxylated units comprised between 2 and 50.

Useful emulsifiers are notably the following products, all marketed by Rhodia:

Soprophor® TSP/724: a surfactant based on ethopropoxylated tristyrylphenol

Soprophor® 796/O: a surfactant based on ethopropxylated tristyrlphenol

Soprophor® CY 8: a surfactant based on ethoxylated tristyrylphenol

Soprophor® BSU: a surfactant based on ethoxylated tristyrylphenol

Alkamuls® RC: a surfactant based on ethoxylated castor oil

Alkamuls® OR/36: a surfactant based on ethoxylated castor oil

Alkamuls® T/20: a surfactant based on sorbiton ester

The formulation advantageously comprises at least 4%, preferably at least 5%, preferably at least 8%, by weight of dry material, of at least one surfactant c).

It is mentioned that the solvent may be combined with an aromatic and/or non-aromatic surfactant.

Other Details as to the Phytosanitary Formulation

The concentrated phytosanitary formulation preferably does not comprise large amounts of water. Typically the water content is less than 50% by weight, advantageously less than 25% by weight. It will be generally less than 10% by weight.

The formulation is preferably a liquid formulation, for example in the form of an emulsifiable concentrate (EC), of a concentrated emulsion (EW) or a micro-emulsion (ME). In this case, it preferably comprises less than 500 g/L of water, more preferably less than 250 g/L. It will generally be less than 100 g/L.

The formulations may advantageously comprise:

a) from 4 to 60%, preferably from 10 to 50% of the phytosanitary product, by weight of active material, b) from 10 to 92%, preferably from 20 to 80%, of the solvent by weight, c) from 4 to 60%, preferably from 5 to 50%, preferably from 8 to 25% by weight of dry material, of an emulsifier, preferably a surfactant, d) from 0 to 10% by weight of water.

Making solid formulations is not excluded, for example formulations in which a liquid comprising the phytosanitary product solubilized in the solvent, is supported by a mineral and/or dispersed in a solid matrix.

The formulation may of course comprise other ingredients (or "other additives"), other than the active phytosanitary product, the solvent(s), the optional emulsifying agent(s) and the optional water. It may notably comprise agents for modifying the viscosity, anti-foam agents, notably silicone anti-foam agents, anti-drift agents, anti-leaching agents, inert fillers, notably mineral fillers, anti-freeze agents.

Notably, the formulations may comprise additives, so-called other additives, not entering the definition of the products a), b), or c), such as:

other solvents, generally in small amounts, i.e. in an amount less than that of the solvent of the solvating system being present in the smallest amount. Another solvent is not meant to be part of the solvating system. As other solvents, mention may notably be made of solvents of the family of phosphates, phosphonates or phosphine oxides such as TEBP, TBP, TEPO, DBBP. Mention is also made of alkyldimethylamides where the alkyl is a $C_6$-$C_{18}$ alkyl, notably those marketed under the brand of Genagen. Mention is also made of ester lactates, notably those marketed under the brand of Purasolv. Mention is also made of fatty acid methyl esters, notably those marketed under the brand of Phytorobe. Mention is also made of diesters of diacids (DiBasic Esters), notably those marketed by Rhodia under the brands of Rhodiasolv RPDE, and Rhodiasolv DIB. Mention is also made of hydrocarbon cuts, cyclic amides such as NMP lactones. Mention is also made of the bis(dialkylamides) described in document WO 2008/074837.

crystallization inhibitors. These may be the solvents mentioned above. These may also be non-polyalkoxylated fatty alcohols or fatty acids. Mention is for example made of the product Alkamuls® OL700 marketed by Rhodia.

Standard methods for preparing phytosanitary formulations or mixtures of solvents may be applied. It is possible to operate by simply mixing the constituents.

The concentrated phytosanitary formulation is intended to be distributed over a cultivated field or a field to be cultivated, for example a soya field, most often after dilution in water, in order to obtain a diluted composition. The dilution is generally performed by the farmer, directly in a tank ("tank mix"), in the tank of a device intended to distribute the composition. This does not exclude addition by the farmer of other phytosanitary products, for example fungicides, herbicides, pesticides, insecticides, fertilizers. Thus, the formulation may be used for preparing a composition diluted in water of the active phytosanitary product, by mixing at least one portion by weight of concentrated formulation with at least 10 parts of water, preferably less than 1,000 parts. The dilution levels and the amounts to be applied on the field generally depend on the phytosanitary product and on the desirable dose for treating the field; this may be determined by the farmer.

Other details or advantages may appear upon considering the example which follow, without any limitation.

EXAMPLES

Example 1.1

Preparation of $CH_3$—CH(O-Me)-$CONMe_2$

The synthesis route is the following:
First Step

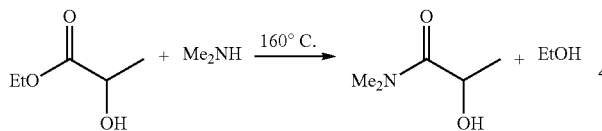

Second Step

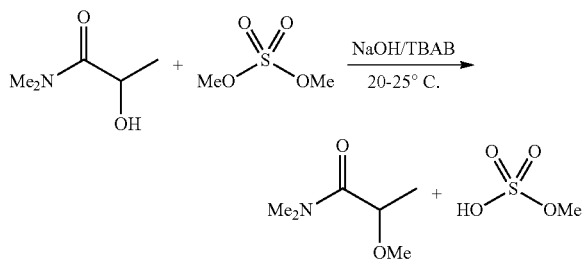

First Step:

In a 2 L autoclave, are mixed at +25° C., ethyl lactate (802 g, 6.79 mol, 1 equivalent) and N,N-dimethylamine (380 g, 8,046 mol, 1.2 equivalents). The mixture is heated to +160° C. under pressure for 16 hours. The crude reaction product is purified by distillation under reduced pressure (P<1 mbar, T vapor=55-56° C.). The dimethyl-lactamide (538 g) is thus obtained with a purity>99%. This corresponds to a yield of the order of 69-70%.

Second step:

In a 3 L flask, are mixed at +25° C., 50% soda in water (240 g, 3 mol, 1.5 equivalents), dichloromethane (1 L) dimethyl-sulfate (378 g, 3 mol, 1.5 equivalent) and tetrabutylammonium bromide (0.5 g, 1.6 mmol, 0.0004 equivalent). To this mixture is added within 1 hour dimethyl-lactamide (234 g, 2 mol, 1 equivalent) at +20° C. The mixture is maintained with strong stirring at this temperature until the dimethyl-lactamide is completely consumed (16 hours). The medium is diluted with water (0.5L). The organic phase is then separated from the water by decantation and the residual aqueous phase is extracted 3 times with 0.5 L of dichloromethane. The organic phases are collected and the solvent is evaporated under reduced vacuum. The reaction crude product is purified by distillation under reduced pressure (P<1 mbar, T vapor=48-50° C.). The desired product (538 g) is thereby obtained with a purity >99%. This corresponds to a yield of the order of 89%.

Example 1.2

Preparation of $CH_3$—CH(O—Cy)—$CONMe_2$

The synthesis route is the following:
First Step
Identical with the first step of Example 1.
Second Step

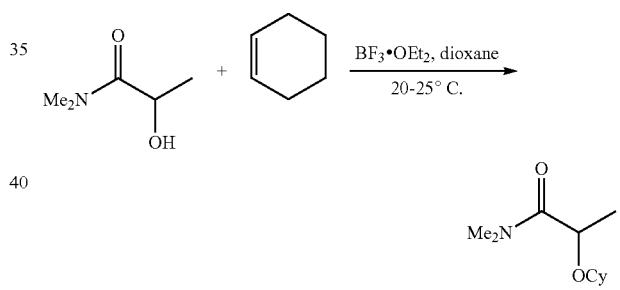

In a 2 L flask, are mixed at +25° C., boron trifluoride etherate (396 g, 2.79 mol, 3 equivalents) and dioxane (0.5 L). To this mixture is added within 1 hour dimethyl-lactamide (109 g, 0.93 mol, 1 equivalent) at +4° C. The mixture is gradually warmed up to +40° C. and then cyclohexene (229 g, 2.79, 3 equivalents) is added within 10 hours with strong stirring at this temperature. The reaction medium is maintained at this temperature until the dimethyl-lactamide is completely consumed (24 hours). The medium, cooled to +20° C., is treated by adding 2N soda until a set pH value is attained, comprised between 6 and 7 (1.2 L). The organic phase is then separated by decantation and the residual aqueous phase is extracted 3 times with 0.75 L of dichloromethane. The organic phases are collected and the solvent is evaporated under reduced vacuum. The reaction crude product is purified by distillation under reduced pressure (P <1 mbar, T vapor=70-74° C.). The desired product (126 g) is thus obtained with a purity >98%. This corresponds to a yield of the order of 68%.

Example 1.3

Preparation of CH₃—CH(O-Ethylhexyl)-CONMe₂

The synthesis route is the following:

First Step

Identical with the first step of Example 1.

Second Step

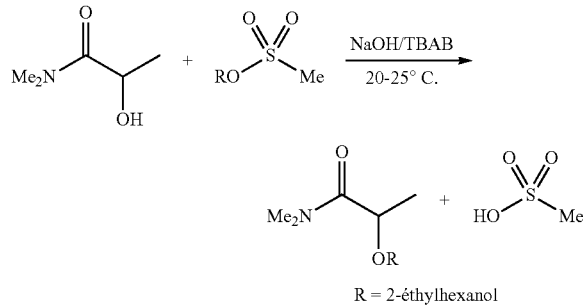

R = 2-éthylhexanol

In a 3 L flask, are mixed at +25° C. 50% soda in water, (248 g, 3.1 mol, 1.5 equivalent), dichloromethane (1 L), 2-ethylhexanol mesylate (prepared beforehand by mesylation of 2-ethylhexanol) (642 g, 3.1 mol, 1.5 equivalent) and tetrabutylammonium bromide (0.5 g, 1.6 mmol, 0.0004 equivalent). To this mixture is added within 1 hour dimethyl-lactamide (241 g, 2.05 mol, 1 equivalent) at +20° C. The mixture is maintained with strong stirring at this temperature until the dimethyl-lactamide is completely consumed (16 hours). The medium is diluted with water (0.5 L). The organic phase is then separated from water by decantation and the residual aqueous phase is extracted 3 times with 0.5 L of dichloromethane. The organic phases are collected and the solvent is evaporated under reduced pressure. The reaction crude product is purified by distillation under reduced pressure (P<1 mbar). The desired product (400 g) is thereby obtained with a purity>99%. This corresponds to a yield of the order of 85%.

| Molecule | Solubility in water (% w/w) |
| --- | --- |
| Example 1.1 | Soluble in all proportions |
| Example 1.2 | 0.4 |
| Example 1.3 | <0.06 |

Examples 2-4

Uses as Solvents of the Compounds of Examples 1.1 to 1.3—Phytosanitary Formulations By mixing the ingredients, formulations of diverse phytosanitary actives are prepared of the emulsifiable concentrate type (EC).

The formulations comprised:

the active, in a weight amount (of active material) as indicated in the table below, 10% by weight of surfactant Alkamuls® RC, marketed by Rhodia and, as a solvent, the remainder of the compound of the examples.

The Examples 2 are comparative examples where the product Rhodiasolv® ADMA10, or Rhodiasolv® ADMA810, from Rhodia (Asia Pacific Zone) is used as a solvent: alkyldimethylamide solvents.

The following tests are conducted:

Visual observation at 25° C., the aspect of the formulation is noted and optionally the presence of crystals is located.

Visual observation at 0° C., the formulation is placed for 7 days at 0° C. and the aspect of the formulation is noted and optionally the presence of crystals is located (CIPAC MT39 test)

Visual observation at 0° C. with nucleation: a crystal of the active material is introduced into the formulation having spent 7 days at 0° C. for nucleation, and the formulation is again placed for 7 days at 0° C. The aspect of the formulation is noted and optionally the presence of crystals is located.

| Example | Solvent | Active | Aspect at 25° C. | Aspect at 0° C. | Aspect at 0° C. with nucleation |
| --- | --- | --- | --- | --- | --- |
| 2.1C | Rhodiasolv ® ADMA 10 | Alachlor - 48% | Limpid | Crystals | Crystals |
| 2.9C | Rhodiasolv ® ADMA 10 | Trifluralin - 40% | Limpid | Limpid | Crystals |
| 2.10C | Rhodiasolv ® ADMA 10 | Difenconazole - 25% | Limpid | Limpid | Crystals |
| 2.12C | Rhodiasolv ® ADMA 10 | Dimethoate - 40% | Cloudy | Cloudy | Crystals |
| 2.13C | Rhodiasolv ® ADMA 10 | Oxyfluorfen - 22% | Limpid | Limpid | Crystals |
| 2.14C | Rhodiasolv ® ADMA 10 | Propoxur - 20% | Limpid | Limpid | Crystals |
| 2.15C | Rhodiasolv ® ADMA 810 | Azoxystrobin - 25% | Non-soluble | Non-soluble | Non-soluble |
| 3.1 | Example 1.1 | Alachlor - 48% | Limpid | Limpid | Crystals |
| 3.2 | Example 1.1 | Chlorpyrifos - 40% | Limpid | Limpid | Limpid |
| 3.3 | Example 1.1 | Alpha-Cypermethrin - 10% | Limpid | Limpid | Limpid |
| 3.4 | Example 1.1 | Phenmedipham 10% | Limpid | Limpid | Limpid |
| 3.5 | Example 1.1 | Propanil - 36% | Limpid | Limpid | Limpid |
| 3.7 | Example 1.1 | Tebuconazol - 25% | Limpid | Limpid | Limpid |
| 3.9 | Example 1.1 | Trifluralin - 40% | Limpid | Limpid | Limpid |

| Example | Solvent | Active | Aspect at 25° C. | Aspect at 0° C. | Aspect at 0° C. with nucleation |
|---------|---------|--------|------------------|-----------------|-------------------------------|
| 3.10 | Example 1.1 | Difenconazole - 25% | Limpid | Limpid | Limpid |
| 3.12 | Example 1.1 | Dimethoate - 40% | Limpid | Limpid | Limpid |
| 3.13 | Example 1.1 | Oxyfluorfen - 22% | Limpid | Limpid | Limpid |
| 3.14 | Example 1.1 | Propoxur - 20% | Limpid | Limpid | Limpid |
| 3.15 | Example 1.1 | Azoxystrobin - 25% | Limpid | Limpid | Limpid |
| 4.1 | Example 1.2 | Alachlor - 48% | Limpid | Limpid | Limpid |
| 4.7 | Example 1.2 | Tebuconazol - 25% | Limpid | Limpid | Limpid |
| 4.9 | Example 1.2 | Trifluralin - 40% | Limpid | Limpid | Limpid |
| 4.10 | Example 1.2 | Difenconazole - 25% | Limpid | Limpid | Limpid |
| 4.13 | Example 1.2 | Oxyfluorfen - 22% | Limpid | Limpid | Limpid |

Example 5

Preparation of 'Linear' Compounds'

The synthesis route is the following:

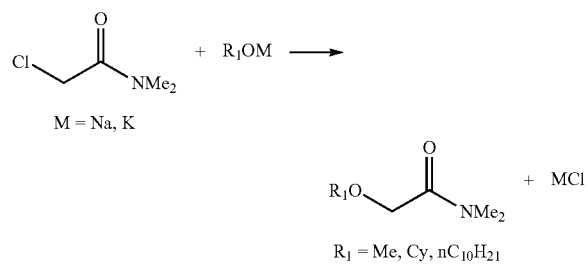

$R_1 = Me, Cy, nC_{10}H_{21}$

Example 5.1

Preparation of $CH_3-O-CH_2-CONMe_2$ (Product 1—$R_1$=Me)

In a 1 liter reactor, initially loaded with sodium methylate in solution in methanol (25% w/w) (682 g, 3.2 mol), with nitrogen inertization, chlorodimethylacetamide (384 g, 3.2 mol) is cast within 2 hours so that the temperature of the reaction medium does not exceed +40° C. At the end of the casing, the temperature of the reaction medium is maintained at +40° C. for 2 hours. After the temperature of the reaction medium has returned to +25° C., the formed salts are removed from the mixture by filtration and the solvents are distilled under partial vacuum. The desired product of 760 g is then obtained.

Example 5.2

Preparation of $Cy-O-CH_2-CONMe_2$ (Product 2—$R_1$=Cy)

Cyclohexanol (12.2 g, 0.11 mol) and toluene (42.2 g) are loaded In a 250 mL reactor. The temperature of this mixture is brought to 30° C. Soda (5.6 g, 0.14 mol) is then introduced with portions of about 2 g. The reaction mixture is mechanically stirred. After maintaining the stirring for ten minutes at 30° C., chlorodimethylacetamide (11.6 g, 0.09 mol) is added dropwise directly into the mass within 0.5 hour. The reaction medium is maintained with stirring at 30° C. for 5 hours. Distilled water is introduced until the totality of the salts are dissolved (about 30 mL). The organic phase is recovered and the solvents are distilled under partial pressure and the desired product is obtained, 12 g, with a yield of 72%.

Example 5.3

Preparation of $nC_{10}H_{21}-O-CH_2-CONMe_2$ (Product 3—$R_1$=$nC_{10}H_{21}$)

In a 250 mL reactor, under a nitrogen atmosphere, is introduced sodium hydride, (60% suspended in mineral oil) (5 g, 125 mmol). This product is washed with pentane (3×15 mL) and is then suspended in THF (100 g). The suspension is cooled to 0° C., n-decanol (17.4 g, 110 mmol) is introduced with a syringe. The chlorodimethylacetamide (12.1 g, 100 mmol) is then slowly added onto the mixture. The temperature of the reaction mixture is brought back to room temperature and the reaction mixture is maintained with stirring for 20 hours. The reaction mixture is neutralized with cold water (20 mL) and then this aqueous phase is extracted with dichloromethane (200 mL), the organic phase is washed with a saturated solution of $NH_4Cl$ (50 mL), a saturated solution of $NaHCO_3$ (50 mL) and then with water (50 mL). The organic phase is dried on sodium sulfate and concentrated under reduced pressure in order to obtain 20.6 g of the expected product with a purity>98% i.e. a yield of 82%.

| Molecule | Solubility in water (% w/w) |
|----------|------------------------------|
| Product 1 | Comprised between 1 and 5 |
| Product 2 | <0.1 |
| Product 3 | <0.1 |

Example 6

Solvating Power of the Agricultural Active Ingredients

Product 1

| Formulations | @ 25° C. | @ 0° C. | @ 0° C. with nucleation |
|--------------|----------|---------|-------------------------|
| Alachlor 48% EC | Limpid | Limpid | Limpid |
| Chlorpyrifos 40% EC | Limpid | Limpid | Limpid |
| Alpha-cypermethrin 10% EC | Limpid | Limpid | Limpid |
| Phenmedipham 16% EC | Limpid | Limpid | Limpid |
| Propanil 36% EC | Limpid | Limpid | Limpid |
| Pendimethalin 33% EC | Limpid | Crystal | **** |
| Tebuconazole 25% EC | Limpid | Limpid | Limpid |
| Triadimenol 23% EC | Cloudy | Cloudy | Cloudy |
| Trifluralin 40% EC | Limpid | Limpid | Limpid |

-continued

| Formulations | @ 25° C. | @ 0° C. | @ 0° C. with nucleation |
|---|---|---|---|
| Difenconazole 25% EC | Limpid | Limpid | Limpid |
| Imidacloprid 20% EC | Limpid | Crystal | **** |
| Oxyfluorfen 22% EC | Limpid | Limpid | Limpid |
| Propuxur 20% EC | Limpid | Limpid | Limpid |

Product 2

| Formulations | @ 25° C. | @ 0° C. | @ 0° C. with nucleation |
|---|---|---|---|
| Alachlor 48% EC | Limpid | Limpid | Crystal |
| Chlorpyrifos 40% EC | Limpid | Limpid | Limpid |
| Alpha-Cypermethrin 10% EC | Limpid | Limpid | Limpid |
| Phenmedipham 16% EC | Limpid | Limpid | Limpid |
| Propanil 36% EC | Limpid | Limpid | Limpid |
| Pendimethalin 33% EC | Limpid | Crystal | = |
| Tebuconazole 25% EC | Limpid | Limpid | Limpid |
| Triadimenol 23% EC | Limpid | Cloudy | Limpid |
| Trifluralin 40% EC | Limpid | Limpid | Limpid |
| Difenconazole 25% EC | Limpid | Limpid | Limpid |
| Oxyfluorfen 22% EC | Limpid | Limpid | Limpid |
| Propuxur 20% EC | Limpid | Limpid | Limpid |

Product 3

| Formulations | @ 25° C. | @ 0° C. | @ 0° C. with nucleation |
|---|---|---|---|
| Alachlor 48% EC | Limpid | Crystal | = |
| Chlorpyrifos 40% EC | Limpid | Limpid | Limpid |
| Phenmedipham 16% EC | Limpid | Limpid | Limpid |
| Propanil 36% EC | Limpid | Crystal | = |
| Tebuconazole 25% EC | Limpid | Limpid | Limpid |
| Triadimenol 23% EC | Cloudy | Crystal | = |
| Trifluralin 40% EC | Limpid | Limpid | Limpid |
| Difenconazole 25% EC | Limpid | Limpid | Limpid |
| Oxyfluorfen 22% EC | Limpid | Crystal | = |

Example 7

Preparation of 'Branched' Compounds

Example 7.1

$R^a$=n-butyl and $R^b$=H and $R^1$=Me (Product 4)

Step 1:

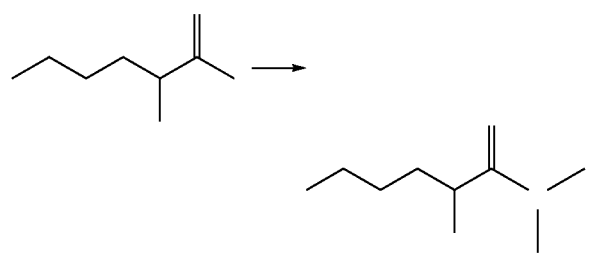

In a three-neck flask at 20° C. and under an inert atmosphere, are mixed ethyl 2-hydroxycaproatel (24.24 g; 150 mmol) and sodium methylate in solution in methanol (25% w/w) (1.6 g; 7 mmol). To this mixture, is added dimethylamine in solution in methanol (50% w/w) (26.75 g; 297 mmol) within 30 minutes. The temperature of this mixture is brought to 40° C. and maintained for 3 hours. After returning of the temperature of this reaction mixture to 20° C., orthophosphoric acid is added until a pH of 5 is obtained. The salts formed are removed by filtration and the solvents are removed under reduced pressure. 2-hydroxy-N,N-dimethylhexanamide is then obtained with a purity of 98% i.e. a yield of 81%.

Step 2:

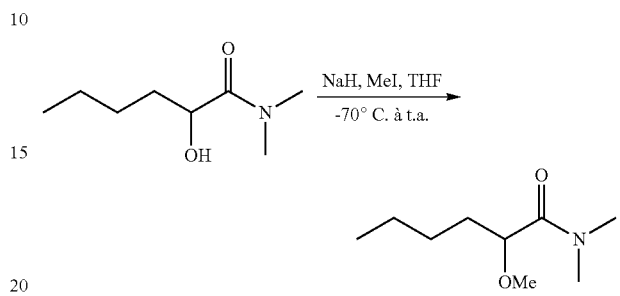

In a three-neck flask, provided with an isobaric addition funnel, with a nitrogen inlet and two septa, sodium hydride (60% suspended in mineral oil) (1.32 g, 33 mmol) is introduced. The product is washed with pentane (3×15 mL) and then suspended in THF (148 g). The suspension is cooled down to −70° C. 2-hydroxy-N,N-dimethylhexanamide (4.45 g, 30 mmol) is introduced with a syringe. Iodomethane (5.89 g, 41 mmol) is then slowly added onto the mixture. The temperature of the reaction mixture is brought to room temperature and the reaction mixture is maintained with stirring for 20 hours. The reaction mixture is neutralized with cold water (20 mL) and then this aqueous phase is extracted with diethyl ether (200 mL). The organic phase is washed with a saturated solution of $NH_4Cl$ (50 mL), a saturated solution $NaHCO_3$ (50 mL) and then with water (50 mL). The organic phase is dried on sodium sulfate and concentrated under reduced pressure in order to obtain 3.75 g of the expected product with a purity >98% i.e. a yield of 77%.

Example 7.2

$R^a$=n-butyl and $R^b$=H et $R^1$=Et (product 5)

Step 1: (Same Product 4)

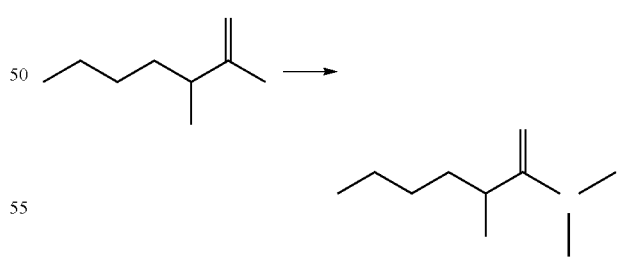

In a three-neck flask, at 20° C. and under an inert atmosphere, are mixed ethyl 2-hydroxycaproate (24.24 g; 150 mmol) and sodium methylate in solution in methanol (25% w/w) (1.6 g; 7 mmol). To this mixture, is added dimethylamine in solution in methanol (50% w/w) (26.75 g; 297 mmol) within 30 minutes. The temperature of this mixture is brought to 40° C. and maintained for 3 hours. After the return of the temperature of this reaction mixture to 20° C., orthophosphoric acid is added until a pH of 5 is obtained. The salts formed are removed by filtration and the solvents are removed under reduced pressure. 2-hydroxy-N,N-dimethylhexanamide is then obtained with a purity of 98%, i.e. a yield of 81%.

Step 2:

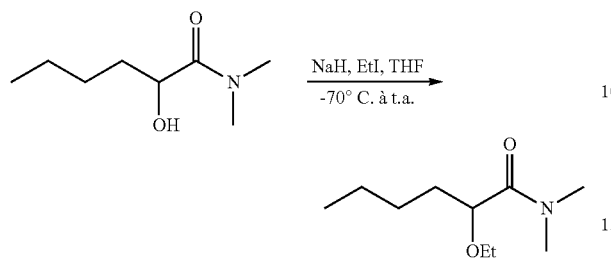

In a three-neck flask, provided with an isobaric addition funnel, a nitrogen inlet and two septa, sodium hydride (60% suspended in mineral oil) (1.09 g, 27 mmol) is introduced. This product is washed with pentane (3×15 mL) and then suspended in THF(140 g). The suspension is cooled down to −70° C. The 2-hydroxy-N,N-dimethylhexanamide (4.36 g, 30 mmol) is introduced with a syringe. Iodethane (6.40 g, 41 mmol) is then slowly added onto the mixture. The temperature of the reaction mixture is brought back to room temperature and the reaction mixture is maintained with stirring for 20 hours. The reaction mixture is neutralized with cold water (20 mL) and this aqueous phase is then extracted with diethyl ether (200 mL). The organic phase is washed with a saturated solution of NH$_4$Cl (50 mL), a saturated solution of NaHCO$_3$ (50 mL) and then with water (50 mL). The organic phase is dried on sodium sulfate and concentrated under reduced pressure in order to obtain 3.4 g of the expected product with a purity >98% i.e. a yield of 52%.

Example 7.3

R$^a$=n-propyl and R$^b$=H et R$^1$=Me (product 6)

Step 1:

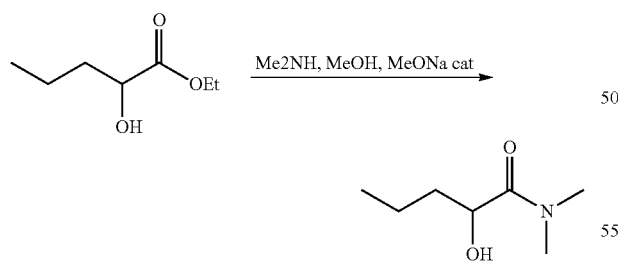

In a three-neck flask, at 20° C. and under an inert atmosphere, are mixed ethyl 2-hydroxyvalerate (31 g; 210 mmol) and sodium methylate in solution in methanol (25% w/w) (2.2 g; 10 mmol). To this mixture, is added dimethylamine in solution in methanol (50% w/w) (37.1 g; 411 mmol) within 30 minutes. The temperature of this mixture is brought to 40° C. and maintained for 3 hours. After return of the temperature of the reaction mixture to 20° C., orthophosphonic acid is added until a pH of 5 is obtained. The salts formed are removed by filtration and the solvents are removed under reduced pressure. 2-hydroxy-N,N-dimethylhexanamide is then obtained with a purity <98% i.e. a yield of 80%.

Step 2:

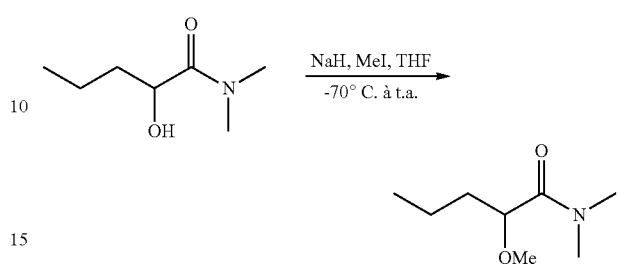

In a three-neck flask, provided with an isobaric addition funnel, with a nitrogen inlet and with two septa, sodium hydride (60% suspended in mineral oil) (1.76 g, 44 mmol) is introduced. This product is washed with pentane (3×15 mL) and then suspended in THF. The suspension is cooled down to −70° C. 2-hydroxy-N,N-dimethylpentanamide (5.43 g, 40 mmol) is introduced with a syringe. Iodemethane (7.88 g, 55 mmol) is then slowly added onto the mixture. The temperature of the reaction mixture is brought back to room temperature and the reaction mixture is maintained with stirring for 20 hours. The reaction mixture is neutralized with cold water (20 mL) and this aqueous phase is then extracted with diethyl ether (200 mL). The organic phase is washed with a saturated solution of NH$_4$Cl (50 mL), a saturated solution of NaHCO$_3$ (50 mL) and then with water (50 mL). The organic phase is dried on sodium sulfate and concentrated under reduced pressure in order to obtain 2 g of the expected product with purity>98% i.e. a yield of 36%.

Example 7.4

R$^a$=n-propyl and R$^b$=H et R$^1$=Et (product 7)

Step 1: (same as product 6)

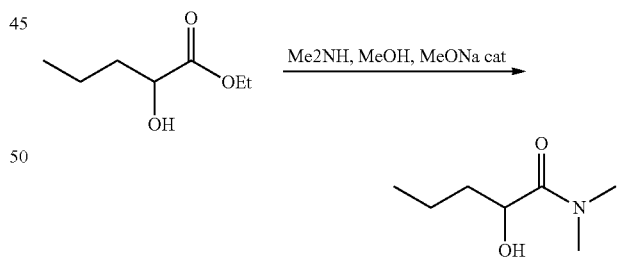

In a three-neck flask, at 20° C. and under an inert atmosphere, are mixed ethyl 2-hydroxyvalerate (31 g; 210 mmol) and sodium methylate in solution in methanol (25% w/w) (2.2 g; 10 mmol). To this mixture, is added dimethylamine in solution in methanol (50% w/w) (37.1 g; 411 mmol) within 30 minutes. The temperature of this mixture is brought to 40° C. and maintained for 3 hours. After return of the temperature of this reaction mixture to 20° C., orthophosphoric acid is added until a pH of 5 is obtained. The salts formed are removed by filtration and the solvents are removed under reduced pressure. 2-hydroxy-N,N-dimethylhexanamide is then obtained with a purity<98% i.e. a yield of 80%.

Step 2:

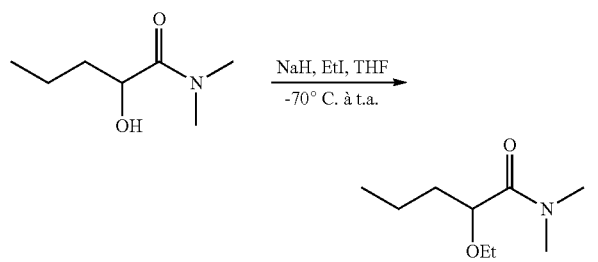

In a three-neck flask, provided with an isobaric addition funnel, with a nitrogen inlet and two septa, sodium hydride (60% suspended in mineral oil) (1.46 g 37 mmol) is introduced. This product is washed with pentane (3×15 mL) and then suspended in THF (184 g). The suspension is cooled down to −70° C. 2-hydroxy-N,N-dimethylpentanamide (5.31 g, 40 mmol) is introduced with a syringe. Iodoethane (8.56 g, 55 mmol) is then slowly added onto the mixture. The temperature of the reaction mixture is brought back to room temperature and the reaction mixture is maintained with stirring for 20 hours. The reaction mixture is neutralized with cold water (20 mL) and then this aqueous phase is extracted with diethyl ether (200 mL). The organic phase is washed with a saturated solution of $NH_4Cl$ (50 mL), a saturated solution of $NaHCO_3$ (50 mL) and with water (50 mL). The organic phase is dried on sodium sulfate and concentrated under reduced pressure in order to obtain 4 g of the expected product with a purity >98% i.e. a yield of 67%.

| Molecule | Solubility in water (% w/w) |
| --- | --- |
| Product 4 | <0.05 |
| Product 5 | <0.05 |
| Product 6 | <0.1 |
| Product 7 | <0.1 |

The invention claimed is:

1. A method of using a compound as a solvent, a co-solvent, a crystallization inhibitor, or a plasticizer, wherein the method comprises using a compound of formula (I):

$$R^a R^b C(OR^1)\text{—}CONR^2 R^3 \quad (I)$$

wherein
$R^a$ and $R^b$, either identical or different, are groups selected from hydrogen and a linear or branched $C_1$-$C_6$ alkyl groups,
$R^1$ is a group $R^{i1}$ or -$(AO)_n R^{i1}$, wherein
$R^{i1}$ is a group selected from hydrocarbon groups comprising an average number of carbon atoms, ranging from 1 to 15, optionally substituted, selected from saturated or unsaturated, linear or branched, acyclic aliphatic groups, saturated, unsaturated or aromatic, monocyclic or polycyclic, carbocyclic or heterocyclic groups and the linkings of said groups,
AO, either identical or different, represents a group of formula —$CH_2$—$CH_2$—O—, —CHMe-$CH_2$—O—, or —$CH_2$—CHMe-O—,
n is an average number greater than or equal to 0,
$R^2$ and $R^3$, either identical or different, are hydrocarbon groups comprising an average number of carbon atoms, ranging from 1 to 15, optionally substituted, selected from saturated or unsaturated, linear or branched, acyclic aliphatic groups, saturated, unsaturated or aromatic, monocyclic or polycyclic, carbocyclic or heterocyclic groups and the linkings of said groups, and
$R^2$ and $R^3$ can optionally form together a cycle, comprising a nitrogen atom to which they are bound, optionally substituted and/or optionally comprising an additional heteroatom,
with the proviso that if $R^a=R^b=H$, the compound of formula (I) is used in a phytosanitary formulation.

2. A method of using a compound as a solvent, a co-solvent, a crystallization inhibitor, or a plasticizer, wherein the method comprises using a compound of formula (I):

$$R^a R^b C(OR^1)\text{—}CONR^2 R^3 \quad (I)$$

wherein
$R^a$ is a linear or branched $C_1$-$C_6$ alkyl group,
$R^b$ is H or a linear or branched $C_1$-$C_6$ alkyl group,
$R^1$ is a group $R^{i1}$ or -$(AO)_n R^{i1}$, wherein
$R^{i1}$ is a group selected from hydrocarbon groups comprising an average number of carbon atoms, ranging from 1 to 15, optionally substituted, selected from saturated or unsaturated, linear or branched, acyclic aliphatic groups, saturated, unsaturated or aromatic, monocyclic or polycyclic, carbocyclic or heterocyclic groups and the linkings of said groups,
AO, either identical or different, represents a group of formula —$CH_2$—$CH_2$—O—, —CHMe-$CH_2$—O—, or —$CH_2$—CHMe-O—
n is an average number are greater than or equal to 0,
$R^2$ and $R^3$, either identical or different, are hydrocarbon groups comprising an average number of carbon atoms, ranging from 1 to 15, optionally substituted, selected from saturated or unsaturated, linear or branched, acyclic aliphatic groups, saturated, unsaturated or aromatic, monocyclic or polycyclic, carbocyclic or heterocyclic groups and the linkings of said groups, and
$R^2$ and $R^3$ can optionally form together a cycle, comprising a nitrogen atom to which they are bound, optionally substituted and/or optionally comprising an additional heteroatom.

3. A method of using a compound as a solvent, a co-solvent, a crystallization inhibitor, or a plasticizer in a phytosanitary formulation, wherein the method comprises using a compound of formula (I-1):

$$R^1 O\text{—}H_2 C\text{—}CONR^2 R^3 \quad (I\text{-}1)$$

wherein
$R^1$ is a group $R^{i1}$ or -$(AO)_n R^{i1}$, wherein
$R^{i1}$ is a group selected from hydrocarbon groups comprising an average number of carbon atoms, ranging from 1 to 15, optionally substituted, selected from saturated or unsaturated, linear or branched, acyclic aliphatic groups, saturated, unsaturated or aromatic, monocyclic or polycyclic, carbocyclic or heterocyclic groups and the linkings of said groups,
AO, either identical or different, represents a group of formula —$CH_2$—$CH_2$—O—, —CHMe-$CH_2$—O—, or —$CH_2$—CHMe-O—
n is an average number greater than or equal to 0,
$R^2$ and $R^3$, either identical or different, are hydrocarbon groups comprising an average number of carbon atoms, ranging from 1 to 15, optionally substituted, selected from saturated or unsaturated, linear or branched, acyclic aliphatic groups, saturated, unsaturated or aromatic, monocyclic or polycyclic, carbocyclic or heterocyclic groups and the linkings of said groups, and $R^2$ and $R^3$ can optionally form together a cycle, comprising a nitrogen atom to which they are bound, optionally substituted and/or optionally comprising an additional heteroatom.

4. The method as defined by claim 1, wherein the total number of carbon atoms, excluding groups $R^1$, $R^2$ and $R^3$ is 2, 3, 4, 5, 6, 7 or 8.

5. The method as defined by claim 2, wherein:
$R^a$=Me or Et, and
$R^b$=H.

6. The method as defined by claim 1, wherein $R^2$ and $R^3$, either identical or different, are selected from the group consisting of methyl, ethyl, n-propyl, isopropyl, n-butyl, isobutyl, n-pentyl, amyl, isoamyl, hexyl, a cyclohexyl group, or in that they form together with the nitrogen atom, a morpholine, pyrrolidine, a piperazine and a piperidine group.

7. The method as defined by claim 1, wherein $R^2$ and $R^3$ are methyl groups.

8. The as defined by claim 1, wherein $R^{\prime 1}$ is selected from the group consisting of methyl, ethyl, propyl, isopropyl, n-butyl, isobutyl, n-pentyl, isopentyl, isoamyl, n-hexyl, cyclohexyl, n-octyl, isooctyl, 2-ethylhexyl, decyl, dodecyl, tridecyl, phenyl, 1-phenylethyl, and benzyl groups.

9. The method as defined by claim 1, wherein $R^{\prime 1}$ is selected from the group consisting of methyl, ethyl, propyl, isopropyl, n-butyl, isobutyl, n-pentyl, isopentyl, isoamyl, n-hexyl, cyclohexyl, n-octyl, isooctyl, 2-ethylhexyl, decyl, dodecyl, tridecyl and 1-phenylethyl groups.

10. The method as defined by claim 1, wherein the compound has a melting point of less than or equal to 20° C.

11. The method as defined by claim 1, wherein the compound has one of the following formulae:

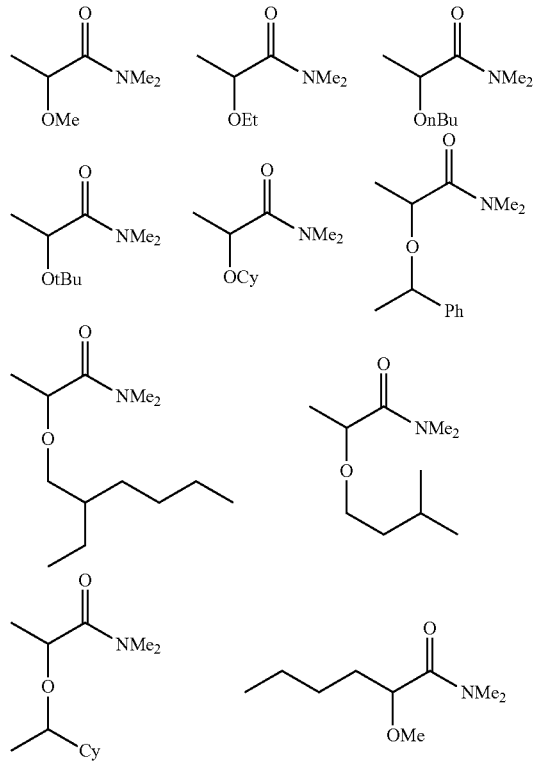

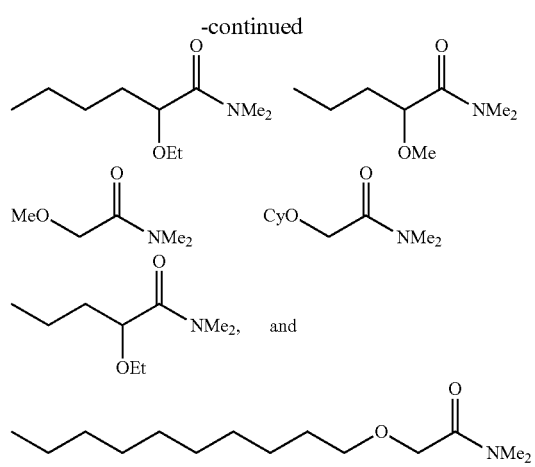

wherein Cy represents a cyclohexyl group.

12. The method as defined by claim 1, wherein the compound is used in a phytosanitary formulation, in a cleaning formulation, in a stripping formulation, in a lubricant formulation, in a coating formulation, in a formulation of pigments or ink, or in a plastic formulation.

13. A compound of the following formula (I):

$$R^a R^b C(OR^1)\text{---}CONR^2 R^3 \qquad (I)$$

wherein
$R^a$ is a linear or branched $C_1$-$C_6$ alkyl group,
$R^b$ is H or a linear or branched $C_1$-$C_6$ alkyl group,
$R^1$ is a group $R^{\prime 1}$ or -$(AO)_n R^{\prime 1}$, wherein
$R^{\prime 1}$ is a group selected from hydrocarbon groups comprising an average number of carbon atoms, ranging from 1 to 15, optionally substituted, selected from saturated or unsaturated, linear or branched, acyclic aliphatic groups, saturated, unsaturated or aromatic, monocyclic or polycyclic, carbocyclic or heterocyclic groups and the linkings of said groups,
AO, either identical or different, represents a group of formula —$CH_2$—$CH_2$—O—, —$CHMe$-$CH_2$—O—, or —$CH_2$—$CHMe$-O—
n is an average number greater than or equal to 0,
$R^2$ and $R^3$, either identical or different, are hydrocarbon groups comprising an average number of carbon atoms, ranging from 1 to 15, optionally substituted, selected from saturated or unsaturated, linear or branched, acyclic aliphatic groups, saturated, unsaturated or aromatic, monocyclic or polycyclic, carbocyclic or heterocyclic groups and the linkings of said groups, and
$R^2$ and $R^3$ may can optionally form together a cycle, comprising the a nitrogen atom to which they are bound, optionally substituted and/or optionally comprising an additional heteroatom, and
with the following conditions:
if $R^a$=Me and $R^b$=H, then $R^1$ is a group different from methyl, n-butyl, benzyl or t-butyl groups.

14. The compound as defined by claim 13, wherein $R^a$ is a linear or branched $C_1$-$C_3$ alkyl group, and $R^b$ is H or a linear or branched $C_1$-$C_3$ alkyl group.

15. The compound as defined by claim 13, wherein:
$R^a$=Me, Et, n-Pr or n-Bu, and
$R^b$=H.

16. The compound as defined by claim 13, wherein $R^2$ and $R^3$ are methyl groups.

17. The compound as defined by claim 13, wherein $R^{\prime 1}$ is selected from the group consisting of ethyl, propyl, isopropyl, n-pentyl, isopentyl, isoamyl, n-hexyl, cyclohexyl, n-octyl, isooctyl, 2-ethylhexyl, decyl, dodecyl, tridecyl and 1-phenyl-ethyl groups.

18. The compound as defined by claim 13, wherein $R^1$ is a methyl or ethyl group.

19. The compound as defined by claim 13, wherein the compound is selected from the group consisting of:

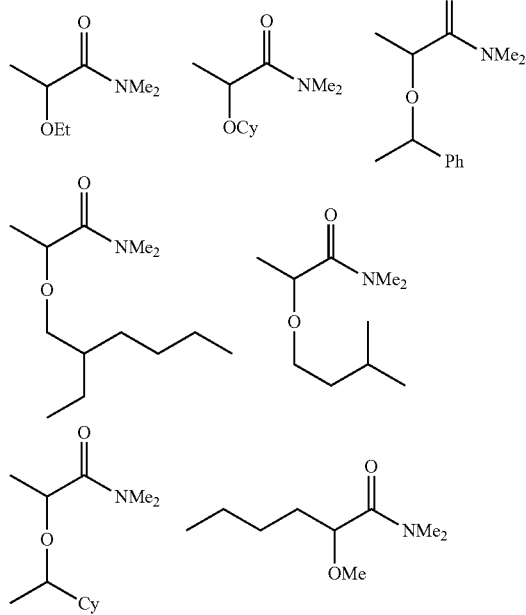

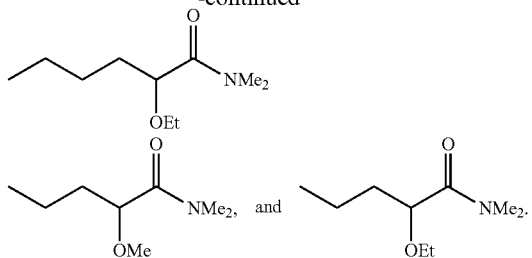

20. The compound as defined by claim 13, wherein the compound is by itself or in a mixture.

21. The method as defined by claim 1, wherein $R^a$ is a $C_1$-$C_3$ alkyl group.

22. The method as defined by claim 2, wherein $R^a$ is a $C_1$-$C_3$ alkyl group.

23. The method as defined by claim 2, wherein $R^b$ is a $C_1$-$C_3$ alkyl group.

24. The method as defined by claim 2, wherein n ranges from 0 to 50.

25. The method as defined by claim 10, wherein the melting point is 5° C.

26. The method as defined by claim 10, wherein the melting point is 0° C.

27. The compound as defined by claim 13, wherein $R^a$ is a $C_1$-$C_3$ alkyl group.

28. The compound as defined by claim 13, wherein $R^b$ is a $C_1$-$C_3$ alkyl group.

* * * * *